(12) United States Patent
DeVito et al.

(10) Patent No.: US 6,242,743 B1
(45) Date of Patent: Jun. 5, 2001

(54) NON-ORBITING TOMOGRAPHIC IMAGING SYSTEM

(75) Inventors: Raymond P. DeVito, Palatine; Edward J. Haines, Marengo; James R. Domnanovich, Elk Grove Village, all of IL (US)

(73) Assignee: Mosaic Imaging Technology, Inc., Schaumburg, IL (US)

( * ) Notice: Subject to any disclaimer, the term of this patent is extended or adjusted under 35 U.S.C. 154(b) by 0 days.

(21) Appl. No.: 09/132,331

(22) Filed: Aug. 11, 1998

(51) Int. Cl.$^7$ .................................................. G01T 1/166
(52) U.S. Cl. ............................. 250/363.05; 250/363.01; 250/363.07
(58) Field of Search .................... 250/363.05, 363.01, 250/363.07, 363.08, 363.09

(56) References Cited

U.S. PATENT DOCUMENTS

| | | | |
|---|---|---|---|
| 4,584,478 | | 4/1986 | Genna et al. . |
| 4,755,680 | * | 7/1988 | Logan ................................. 250/369 |
| 4,833,327 | * | 5/1989 | Hart ................................. 250/363.01 |
| 5,245,190 | | 9/1993 | Sibbald et al. . |
| 5,451,789 | * | 9/1995 | Wong et al. ..................... 250/363.03 |
| 5,534,701 | * | 7/1996 | Pierfitte et al. ................. 250/363.04 |
| 5,670,783 | * | 9/1997 | Ray ................................. 250/363.05 |
| 5,742,060 | | 4/1998 | Ashburn . |
| 5,821,541 | * | 10/1998 | Tumer ............................. 250/370.09 |
| 5,998,792 | * | 12/1999 | DiFilippo ........................ 250/363.05 |
| 6,008,493 | * | 12/1999 | Shao et al. ....................... 250/363.04 |
| 6,020,589 | * | 2/2000 | Plazenet et al. ................ 250/363.04 |

OTHER PUBLICATIONS

Y. Hirose et al., "A Hybrid Emission CT–Headtome II" IEEE Transactions on Nuclear Science, vol. NS–29, No. 1, Feb. 1982, pp. 520–523.

D.–C. Yu et al., "A Study of Reconstruction Accuracy for a Cardiac SPECT System with Multi–Segmental Collimation," IEEE Transactions on Nuclear Science, vol. 44, No. 3, Jun., 1997, pp. 1403–1408.

* cited by examiner

Primary Examiner—Constantine Hannaher
Assistant Examiner—Otilia Gabor
(74) Attorney, Agent, or Firm—Charles F. Meroni, Jr.; Meroni & Meroni, P.C.

(57) ABSTRACT

A tomographic imaging system which images ionizing radiation such as gamma rays or x rays and which: 1) can produce tomographic images without requiring an orbiting motion of the detector(s) or collimator(s) around the object of interest, 2) produces smaller tomographic systems with enhanced system mobility, and 3) is capable of observing the object of interest from sufficiently many directions to allow multiple time-sequenced tomographic images to be produced. The system consists of a plurality of detector modules which are distributed about or around the object of interest and which fully or partially encircle it. The detector modules are positioned close to the object of interest thereby improving spatial resolution and image quality. The plurality of detectors view a portion of the patient or object of interest simultaneously from a plurality of positions. These attributes are achieved by configuring small modular radiation detector with high-resolution collimators in a combination of application-specific acquisition geometries and non-orbital detector module motion sequences composed of tilting, swiveling and translating motions, and combinations of such motions. Various kinds of module geometry and module or collimator motion sequences are possible, and several combinations of such geometry and motion are shown. The geometric configurations may be fixed or variable during the acquisition or between acquisition intervals. Clinical applications of various embodiments of the tomography invention include imaging of the human heart, breast, brain or limbs, or small animals. Methods of using the non-orbiting tomographic imaging system are also included.

92 Claims, 10 Drawing Sheets

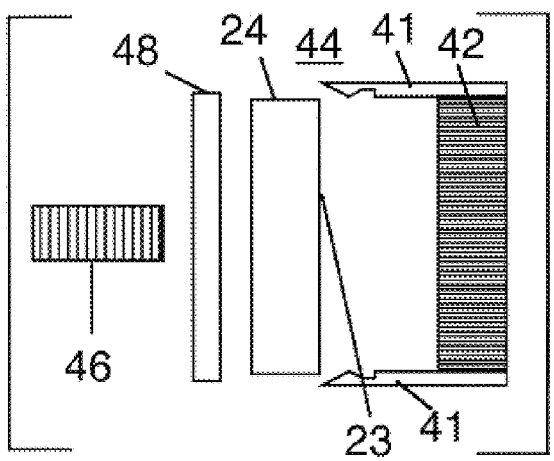
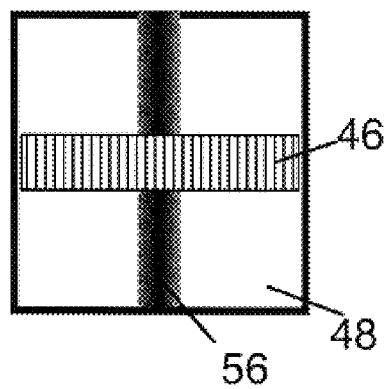
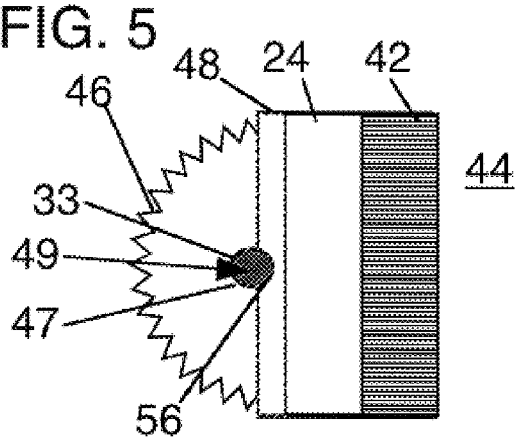
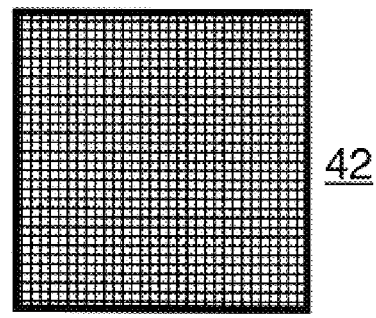
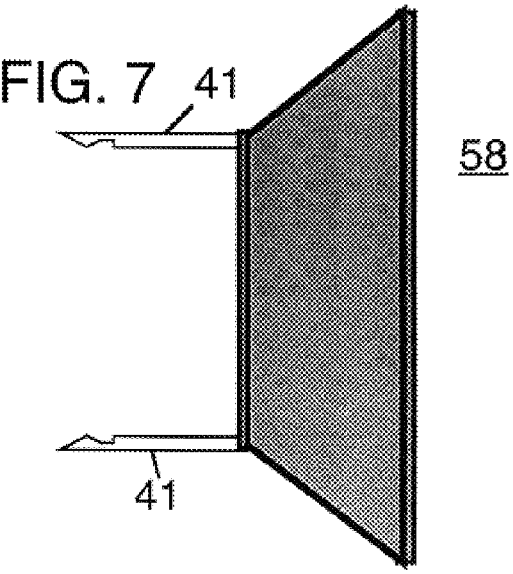

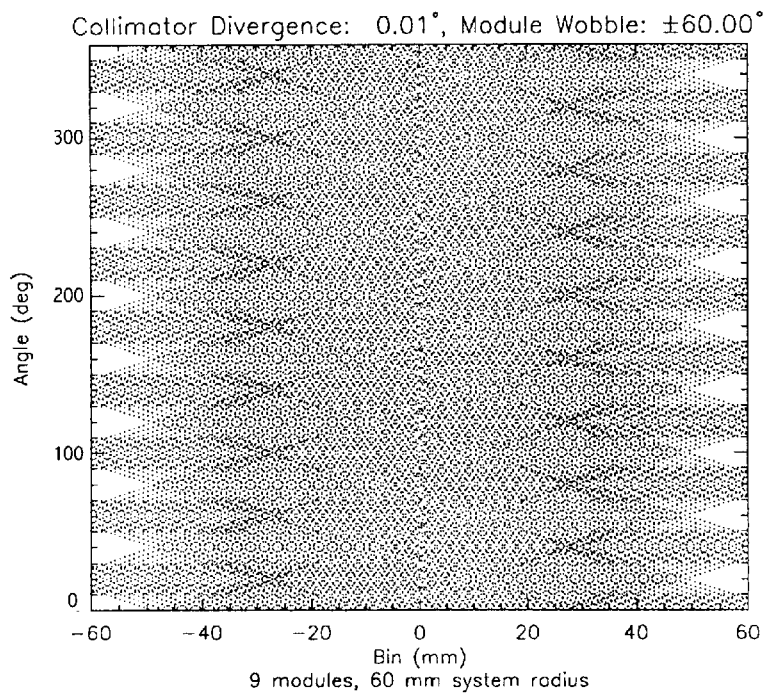
FIG. 13.a
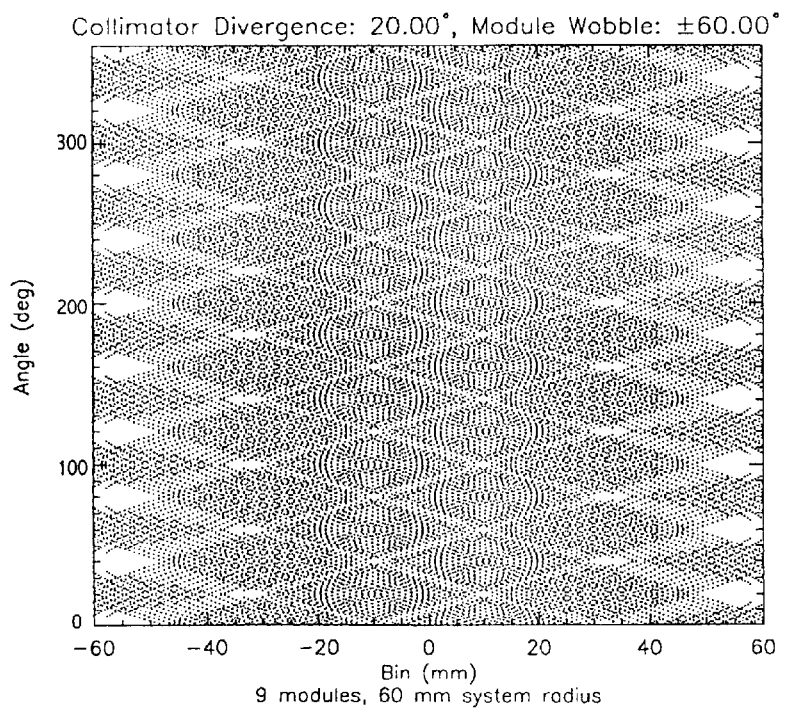
FIG. 13.b

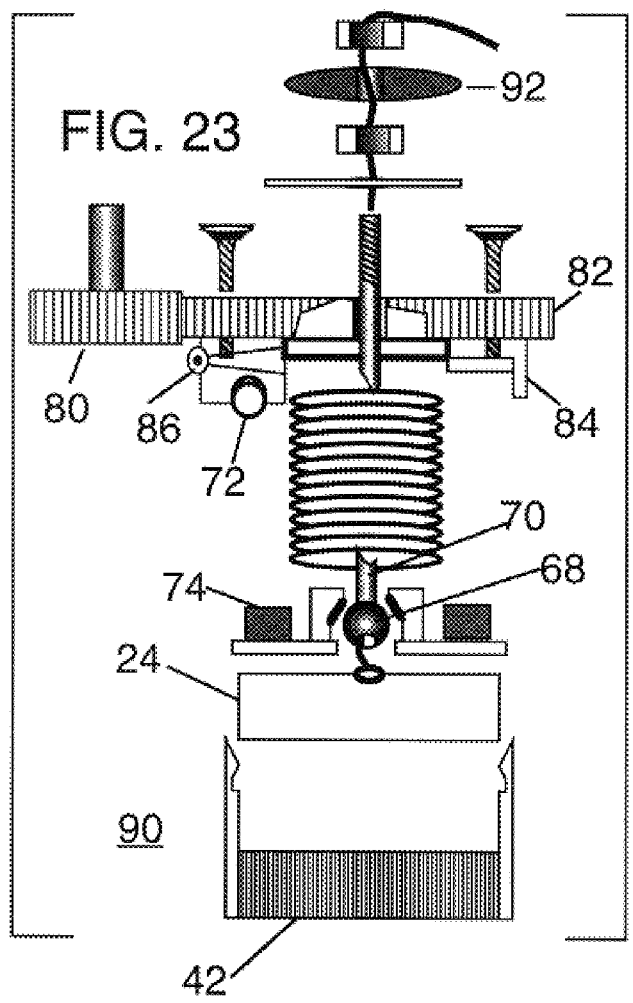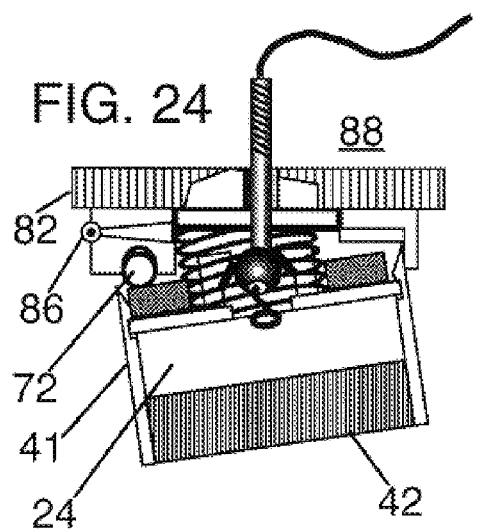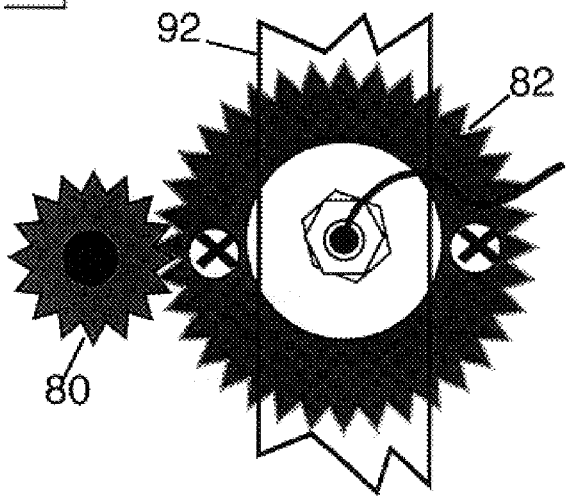

NON-ORBITING TOMOGRAPHIC IMAGING SYSTEM

FIELD OF THE INVENTION

This disclosure relates generally to tomographic imaging and, in particular, relates to a tomographic imaging system for imaging ionizing radiation such as gamma rays or x rays.

BACKGROUND OF THE INVENTION

In conventional gamma cameras such as Anger cameras known in the art, a single radiation detector having a planar surface is employed for detecting gamma rays for tomographic imaging. A radiopharmaceutical or radioisotope, chosen for its affinity for a particular region or metabolic function of interest, is administered to the patient. The radioisotope emits gamma radiation in all directions from the target location or process. Some of the emitted gamma rays leave the body in the direction of the detectors carrying with them information about their location of origin. The sensitivity of conventional gamma cameras to gamma radiation can be increased by employing a multiplicity of detector heads. When performing Single Photon Emission Computed Tomography (SPECT) using such multiple-detector systems, the detectors are caused to orbit the patient or the object of interest in order to sample from many locations around the object the distribution of radioactivity being emitted from the patient or the object of interest. In conventional SPECT using large detectors, the orbiting of the detector or detectors and the sampling of the gamma rays from multiple directions is necessary in order to provide sufficient information to reconstruct a three-dimensional image of the radiation source by means of computed tomography.

In the prior art, the detectors are typically mounted on a gantry to provide structural support and to orbit the detector around the object of interest. The detector is shielded to prevent stray gamma rays (those not originating from the object of interest) from being detected. Between the radiation detector and the object being imaged is a collimator that is used to restrict the acceptance, or the direction of travel, of incident gamma rays. Typically this collimator is constructed to provide a multiplicity of small holes in a dense, high-atomic-number material such as lead. The gamma rays will pass through the holes if they travel in a direction aligned with the hole but will tend to be absorbed by the collimator material if they travel in a direction not aligned with the holes.

Conventional gamma camera detectors used for medical imaging have a large, flat field of view (typically about 300 in$^2$) and are very heavy, typically weighing several hundred pounds. These detectors must be made to orbit the patient or object of interest as close as possible (for best image quality) and with a high degree of accuracy and precision. In the current state of the art, large gantries and powerful motors are required to control and accomplish this motion. The safety of the patient in such systems is always a concern. The size and weight of conventional systems often limit or preclude entirely certain dynamic (or "real-time") imaging procedures that require quickly obtaining views of the patient from sufficiently many directions to allow multiple time-sequenced tomographic images to be produced. Due to their weight and the requirements for accurate detector rotation, conventional tomographic gamma camera systems impose elaborate site requirements and operating conditions and are practically incapable of being relocated to another site. Thus, there is a need for tomographic systems that are mobile, allowing the imaging system to come to the patient rather than forcing the patient to be transported to the imaging system. Often, it is unsafe, inconvenient or impossible to move the patient to the conventional gamma camera system. System mobility can improve diagnostic cost efficiencies and provide better health care as a result of timely, on-the-spot prognosis. Moreover, the economics of medical imaging would be improved if the weight of the system could be reduced and the site conditions for the system could be simplified. Thus, there exists a clinical need for tomographic systems that are smaller, that avail themselves to existing clinical applications as well as emerging special-purpose clinical applications, and which impose less stringent site requirements.

Many of the current problems in nuclear medicine imaging are caused by the large flat face of the conventional detector. The algorithms used to determine the location of the gamma interaction (the gamma event) in Anger cameras favor large, flat crystals. These positioning algorithms break down near the edges of the detector producing a significant "dead margin" of several centimeters around the perimeter of the detector. Not only is the dead margin unable to produce usable information, it makes difficult or impossible several types of clinical acquisition protocols, such as lateral breast imaging adjacent to the chest wall and SPECT imaging of the breast.

One of the major problems in nuclear medicine is the poor spatial resolution in the images. This poor spatial resolution is caused mostly by the collimator, and only slightly by the intrinsic resolution in the detector. The collimator restricts the angle of acceptance of incident gamma rays and thus produces a distance-dependent resolution that grows linearly with distance between the source and detector. Roughly speaking, there is loss of 1 mm in resolution for every 1 cm distance between the source and the detector. Simple geometry and the need to clear the patient during an orbital scan prohibit the entire camera face from approaching the patient. Inevitably, in nearly all SPECT applications, part of the camera face is far from the patient and suffers serious loss of resolution.

One clinical application that can benefit from improved spatial resolution is the detection and diagnosis of breast cancer. X-ray Mammography is the standard procedure used in detecting small non-palpable abnormalities in breast tissue. Although modern x-ray mammography has a sensitivity of nearly 90% for the detection of breast cancers, its specificity (the ability to distinguish malignant from benign tissue) is rather low. Of all the breast biopsies performed because of suspicious x-ray mammograms, only about 11–36% are positive for cancer. The path to final diagnosis, which may typically involve percutaneous fine-needle aspiration, stereotactically guided core biopsy, or surgical excision, is often long, expensive, and emotionally and physically traumatic for the patient. Nuclear Mammography is a promising new technique for the detection of breast cancer. Nuclear Medicine studies are a unique and valuable clinical tool. They can distinguish benign from malignant lesions based on cell metabolism, providing a non-invasive cost-effective intermediate option before resorting to biopsy. In recent years, the importance of Nuclear Mammography and the number of clinical studies performed has grown rapidly.

Nuclear Mammography has been shown to be a promising alternative in the process of locating and diagnosing larger breast lesions. However, Nuclear Mammography with conventional gamma cameras suffers from several drawbacks which severely limit its utility in breast imaging applications. Conventional detectors and collimators lack sufficient spatial resolution to detect and image lesions smaller than about 10 mm. The insensitive "dead margin" near the edge of the detector keeps the useful field of view several centimeters away from the chest wall and limits the amount of the breast that can be imaged laterally. The large size and weight of the detector often limit the clinical applications to lateral planar imaging and preclude medial breast imaging and conventional orbital SPECT of the breast. Tomography would be preferred over planar imaging because SPECT generally provides better lesion contrast.

A need exists for a gamma camera able to perform tomographic imaging without using large detectors or collimators or the orbiting motion of such detectors or collimators. A non-orbiting tomography system composed of smaller detector modules would enable improvements spatial resolution and system sensitivity which would result in improved image quality and diagnostic accuracy. It would also broaden clinical utility, improve patient access to systems, allow better dynamic studies and reduce site requirements.

Several devices or inventions have been made which try to address some of these issues. Wong and Hicks (U.S. Pat. No. 5,451,789), for example, disclose an invention in which uncollimated, stationary detectors perform breast tomography by means of positron emission (dual-photon) tomography (PET). In contrast, the invention disclosed here combines collimation, localized (non-orbiting) detector or module motions, and various module/acquisition geometries to perform tomography of the breast and other objects of interest by means of single-photon emission tomography. Similarly, the system described by Genna et al (U.S. Pat. No. 4,584,478) is based on a collimator which must orbit the object of interest in order to perform tomography. The system described by Ashburn (U.S. Pat. No. 5,742,060), while mobile, is not capable of tomography. The Headtome II device, (as described for instance in "A Hybrid emission CT-Headtome II", by Y. Hirose et al, *IEEE Transactions on Nuclear Science*, Vol. NS-29, No. 1, February, 1982, pp. 520–523), employs orbital and "wobbling" motions of its detector and collimator. However, the wobbling motions are not sufficient for tomography and must be augmented by orbiting detector or collimator motions. An important component of the invention disclosed here is the non-orbital motion of the detectors or collimators which are sufficient for tomography.

SUMMARY OF THE INVENTION

The objectives of the present invention are to 1) provide an imaging system that can produce tomographic images without requiring an orbiting motion of the detector(s) or collimator(s) around the object, 2) produce smaller tomographic systems with enhanced system mobility, and 3) provide a tomographic system for emission imaging capable of observing the object of interest from sufficiently many directions to allow multiple time-sequenced tomographic images to be produced.

These and-other objectives are achieved by a tomographic imaging system consisting of a plurality of detector modules which are distributed about or around the patient or object of interest and which fully or partially encircle it. Each detector module detects ionizing radiation emitted by the object and produces information about the energy and position within the detector module of the interaction event. The plurality of detector modules are positioned close to the object of interest thereby improving spatial resolution and image quality. The plurality of detectors view a portion of the patient or object of interest simultaneously from a plurality of positions. A means is provided to cause the plurality of detector modules to change their position or direction of view of the object A means to determine the location and direction of view of each detector module is also provided. This information, as well as other pertinent information, is provided to a data acquisition computer which reconstructs a tomographic image of the object of interest using a mathematical reconstruction algorithm. Because the detector modules are small, many novel module acquisition geometries, many kinds of novel module motion sequences are possible, and many more combinations of geometry and motion are possible. These combinations comprise the set of embodiments of the invention disclosed here and are described below.

DESCRIPTION OF THE DRAWINGS

FIG. 3 is a an exploded side view of the swiveling detector module used in the embodiment represented in FIG. 1 showing a parallel-hole collimator.

FIG. 4 is a rear plan view of the swiveling detector module shown in FIG. 3.

FIG. 5 is a top plan view of the swiveling detector module shown in FIG. 3.

FIG. 6 is a front plan view of the swiveling detector module shown in FIG. 3 showing a representation of the high-resolution collimator, noting that actual collimators may have a hole patter other than what is shown.

FIG. 7 is a side plan view of a diverging which may be used in place of the parallel-hole collimator shown in FIG. 3.

FIG. 13 contains sinogram plots of the angular coverage of the tomographic projection data generated by two versions of the preferred non-orbital breast tomography embodiment of FIG. 1. FIGS. 13.a and 13.b were generated for parallel-hole and diverging collimation, respectively. Both sinograms were generated for a transverse module swivel arc of −60° to +60°.

FIG. 23 is an exploded side view of a cam-driven detector module assembly (shown here with a parallel-hole collimator) used in the embodiment represented in FIG. 20.

FIG. 24 is a partial sectional side view of a cam-driven detector module assembly shown in FIG. 23.

FIG. 25 is a top view of a cam-driven detector module assembly shown in FIG. 24.

DETAILED DESCRIPTION OF THE INVENTION

Figure 1:
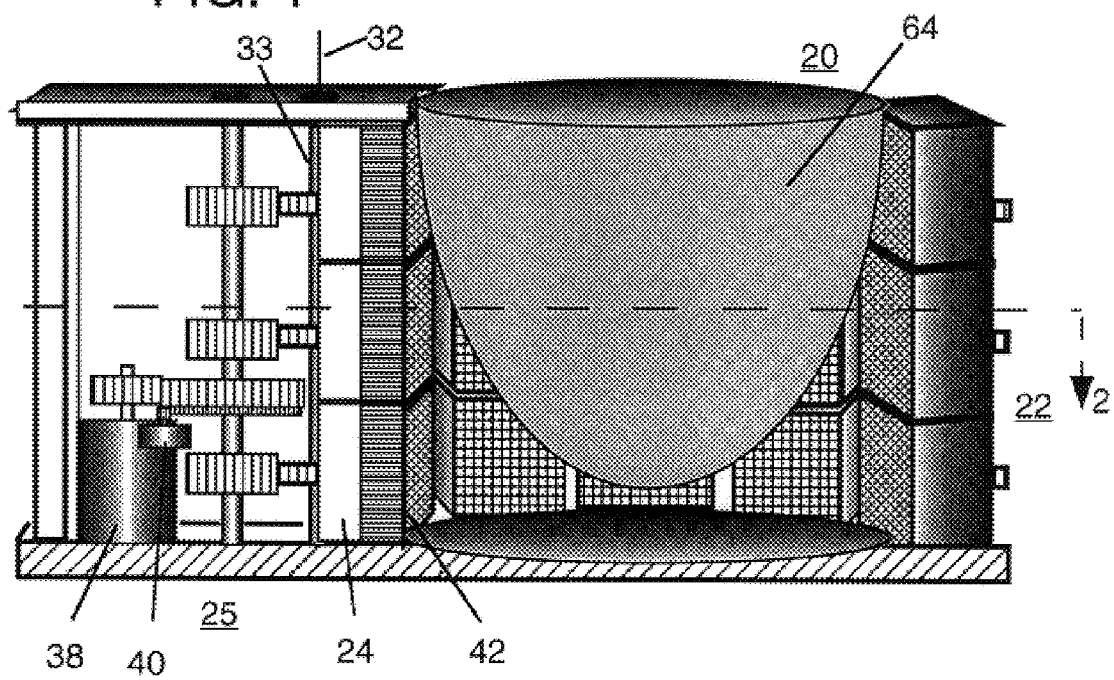
FIG. 1 is a partial side sectional view, taken across line 1—1 in FIG. 2, of the preferred embodiment of the disclosed non-orbital tomography invention in a Nuclear Mammography configuration.
Figure 2:
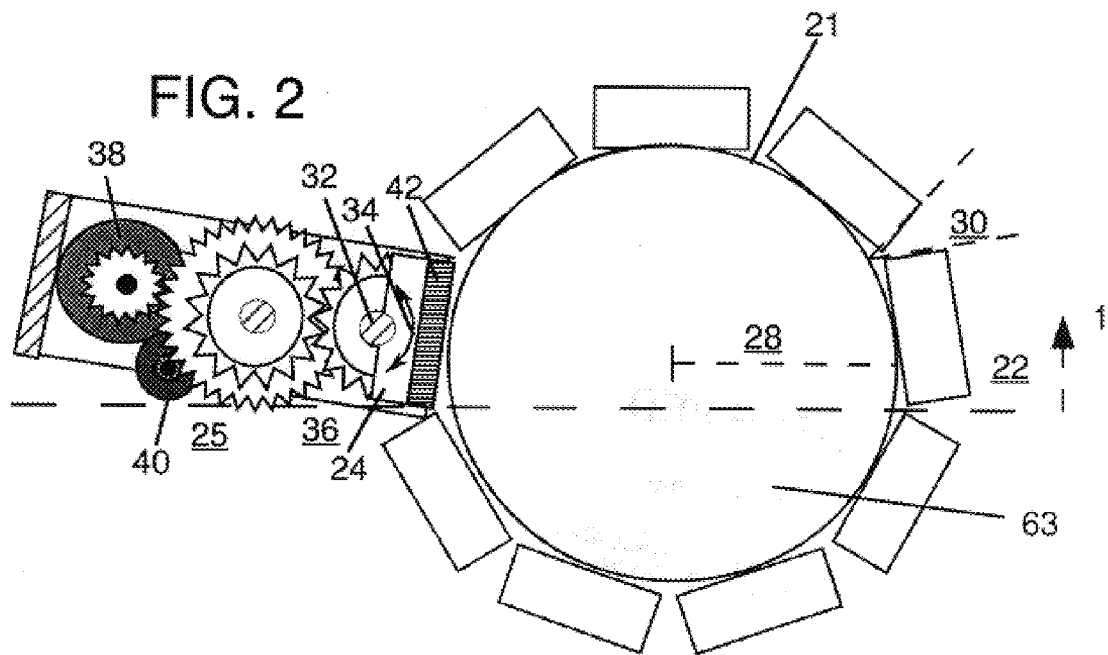
FIG. 2 is a top sectional view, taken across line 2—2 in FIG. 1, of a transverse cross section through a ring of modules of the non-orbital breast tomography embodiment showing the ring structure and the mechanism to vary the viewing direction of the detector modules.
Figure 8:
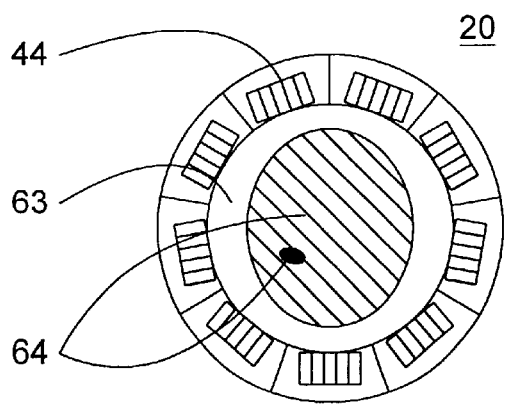
FIG. 8 shows a transverse cross section of the system with an object of interest (a human breast with lesion) in the reconstruction volume.

Various embodiments of the non-orbiting tomographic invention are described here. Each embodiment is able to acquire projection data of a patient or object of interest from multiple directions without the orbital motions associated with conventional tomography. Each embodiment is constructed of small detector modules. Each detector module consists of a photon-sensitive radiation detector, its housing and shielding, and an associated collimator. The collimator restricts the acceptance of gamma rays, discriminated according to their direction of travel, to those whose trajectories are approximately aligned with the collimator holes. The collimator may be removed for testing or calibration purposes. A given collimator may be exchanged with another of different collimation properties to tailor the imaging performance to a particular application. Each radiation detector detects the ionizing radiation and produces information regarding the interaction position within the detector. One possible radiation detector configuration is composed of an array of many small pixels. Such pixels may be defined physically by the construction of the detector (as in the case of a pixellated solid-state detector) or may be defined electronically or computationally using data acquired by the detector (as in the case of a scintillator/photomultiplier-tube detector). The pixels therefore provide the means of locating the event (photon/detector interaction) produced by a an incident photon. Electronics associated with the pixel or the detector convert the energy of the incident photon to an electrical signal which is read out with the photon event location and processed.

The photon-sensitive detector material may be a solid-state (semiconductor) detector material such as Cadmium Zinc Telluride (CZT) or Cadmium Telluride (CdTe), as in the preferred embodiments described below. CZT or CdTe detectors can be produced in the form of pixellated radiation detectors consisting of many individual photon-sensitive pixels. In this form, CZT or CdTe semiconductor detectors are preferred because they combine the most desirable attributes of the three most commonly used gamma-ray and x-ray detector materials (sodium-iodide/photomultiplier-tube, silicon and germanium): compact size, room-temperature operation, position sensitivity, good energy resolution and stopping power. Those skilled in the art recognize that alternative detector choices also produce satisfactory detector characteristics. These alternative choices of material do not alter the basic operation of our system and are considered to be within the scope the present invention. Such alternatives to solid-state (semiconductor) detector materials may include silicon, germanium, mercuric iodide, gallium arsenide or other photon-sensitive solid-state (semiconductor) materials. The detector material may also be a scintillator such as sodium iodide, cesium iodide or another scintillator material.

In the various embodiments of the non-orbiting tomographic invention, several modules are distributed around the patient or object of interest. The direction of view of the modules is varied according to one or more independent degrees of freedom of motion in a manner (described below) which involves tilting, swiveling, rotating or translating the module or collimator, or sequential or simultaneous combinations of such motions. The aim of such motion is to achieve sufficient tomographic sampling of the object of interest such that a perceptibly artifact-free image can be tomographically reconstructed. A means to accomplish such motions is incorporated into the system. However, none of the disclosed embodiments requires that the modules or the collimator orbit the object of interest. A means to determine the location and direction of view of each module and to provide such information to the data acquisition apparatus is also incorporated into the system as shown in the block diagram in FIG. 11. The photon event data (the photon/detector interaction location and photon energy) acquired over a given time interval by a given module at a given location and viewing direction are used to create projection data of the object of interest. By distributing the modules according to one of the module/acquisition geometries described below, and by causing the modules to execute one of the motion sequences described below, projection data of the object of interest are acquired from a plurality of modules and from a plurality of viewing directions of each module. Sufficient information is thereby acquired to allow three-dimensional image reconstruction of the object of interest in various clinical and non-clinical applications by well known mathematical and computational techniques.

Figure 19:
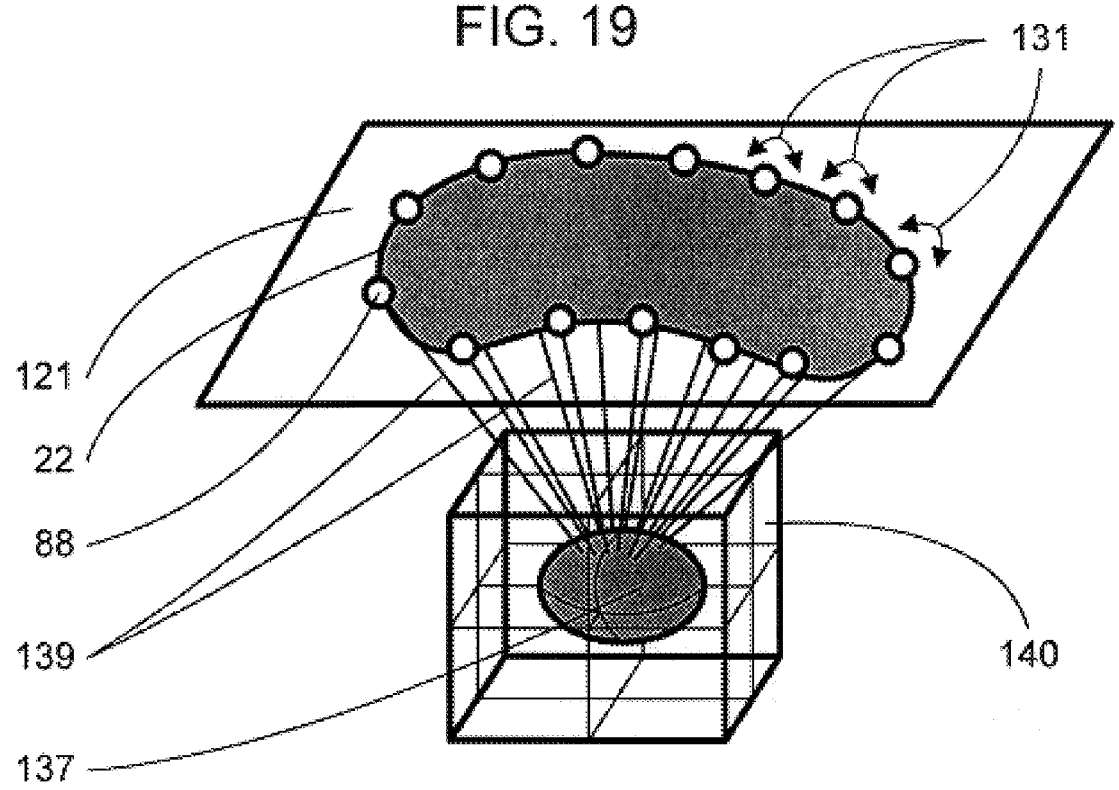
FIG. 19 illustrates the reconstruction volume and detector plane for the out-of-plane viewing associated with an acquisition geometry suitable for ectomographic reconstructions but with non-orbital detector module motions.
Figure 20:
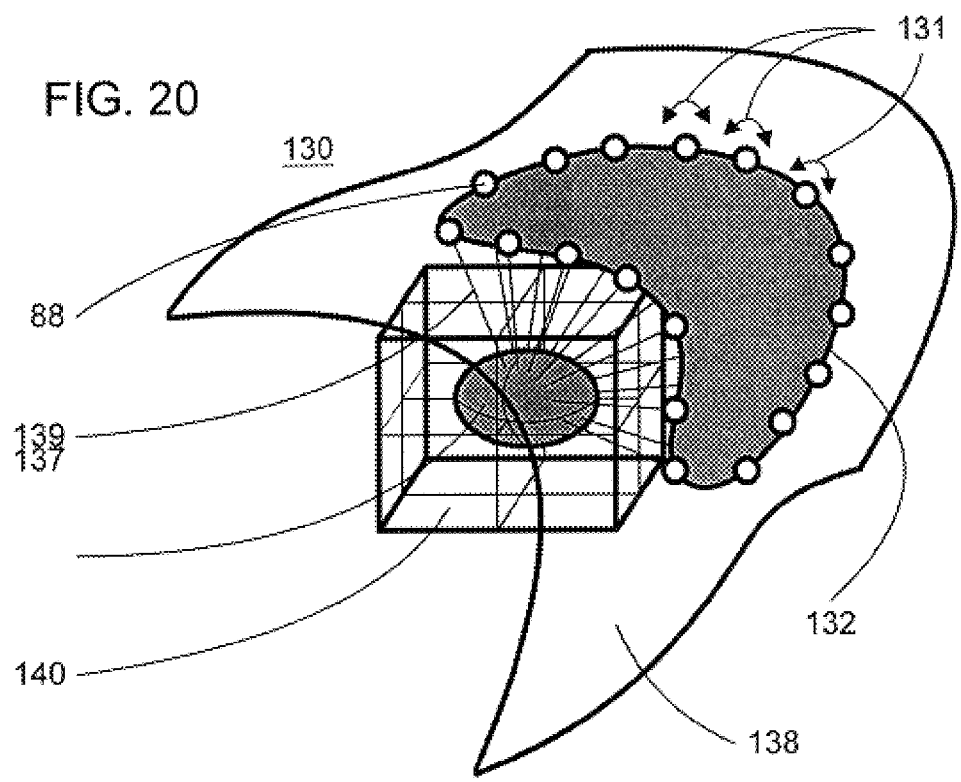
FIG. 20 illustrates the acquisition geometry and reconstruction volume for the non-orbital cardiac imaging embodiment. (See also FIG. 17.) FIGS. 21 and 22 add clarification of the various anatomical components of the drawing.

For the purpose of describing and defining the invention disclosed here, the term reconstruction volume shall refer the object of interest and the neighboring regions surrounding it. The object of interest is the physical object for which the tomographic images are desired. For example, the heart, breast and brain are the objects of interest for cardiac, mammography and brain tomography, respectively. The reconstruction volume is a mathematical or computational region which contains the object of interest in its entirety as well as its surrounding neighboring regions. While the object of interest is usually irregularly shaped, the reconstruction volume is typically chosen to be a mathematically or computationally convenient shape in order to aid the image reconstruction and display processes. For example, the reconstruction volume might be a right circular cylinder (as shown in FIGS. 1, 2, 8, and 14–16) or a cube (as shown in FIGS. 19 and 20).

Primary Aspects of the Invention

There are primarily two distinctive aspects of the disclosed non-orbiting tomography invention: 1) the module or acquisition geometry (the arrangement of the detector modules with respect to the patient or object of interest) and 2) the motion sequences the modules execute in order to acquire the projection data necessary to tomographically reconstruct the object of interest. There are several embodiments possible. Various other aspects of the invention contribute to its uniqueness among the art. For the purpose of further describing and defining the invention, we highlight module/acquisition geometries and the module motions. There are several possible embodiments. Roughly speaking, there is one embodiment of the invention for each of the several possible combinations of 1) the different types of module/acquisition geometry, and 2) the different types of module or collimator motions that can be applied in order to acquire the needed projection data.

Module/Acquisition Geometry

We will now characterize the range of possible geometrical embodiments of the non-orbiting tomographic imaging invention. Each embodiment falls into one of two categories depending on the general type of module/acquisition geometry it embodies: planar or non-planar. These terms are used here to describe the geometry of a set or a subset of the modules in a given embodiment.

The planar module/acquisition geometries consist of one or more sets of modules in which each set of modules lies in a ring. Each such module ring is defined and characterized as follows:

1. The module ring is a set of modules which lie on one or more segments of a ring (the module ring) described by a closed, simply-connected, piecewise continuous curve.
2. The module ring lies in and defines a flat plane (the module plane) which may or may not intersect the computational reconstruction volume,
3. The module ring may encircle the object of interest fully (leaving no substantial gaps around the ring) or partially (leaving one or more substantial gaps around the ring). One or more such module rings are arranged to form fully or partially closed module surfaces which tend to fully or partially encircle or enclose the object of interest, as shown in FIGS. 1, 2, 14–16. Such systems are intended to perform non-orbital tomography on objects of interest which can be readily surrounded or partially surrounded by a set of modules which can be positioned close to the object of interest. Such objects may include the human breast (FIG. 1), head, arm, or leg (FIGS. 14–15), or a small animal (FIG. 16), or other distributions of radioisotope.

Figure 17:
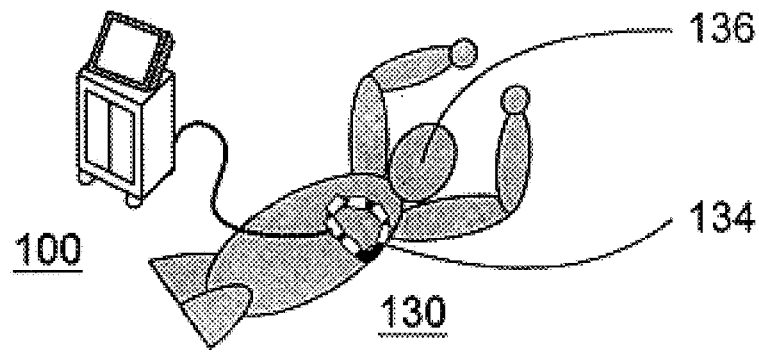
FIG. 17 is a schematic drawing of the disclosed non-orbital tomography invention in a cardiac imaging configuration. See also FIG. 20.

The non-planar module/acquisition geometries consist of one or more sets of modules in which each set comprises an array. Each such module array is defined and characterized as follows:

1. The module array is a set of modules comprising a bounded array which may or may not take the form of a module ring as defined above.
2. The module array lies on a topological manifold (the module manifold) (in this case, a two-dimensional, piece-wise continuous surface in three-dimensional space) which may or may not intersect the computational reconstruction volume.
3. The module array may encircle or enclose the object of interest fully (leaving no substantial gaps around the object) or partially (leaving one or more substantial gaps around the object). One or more such module arrays are arranged to form open module surfaces which tend to wrap partially around the object of interest, as shown in FIG. 20. Open systems are required so that part of the patient or object of interest can be placed within the reconstruction volume of the given embodiment while the remainder lies outside. Such open systems based on non-planar module geometries are intended to perform non-orbital tomography on objects of interest which cannot be easily surrounded by a set of closely positioned modules, such as the human heart (FIG. 17).

Closed module geometries are those in which modules surround the object of interest. Such embodiments can be constructed from one or more module arrays in which the corresponding module manifolds taken together wrap fully around the object of interest, or from module rings arranged to surround the object of interest. Such closed embodiments could be used in applications in which modules can fully surround the object of interest. Such applications include small animal imaging or industrial non-destructive testing or evaluation.

Planar Embodiments

The various possible embodiments of the disclosed planar module/acquisition geometries fall into three subcategories depending on the number of module rings they employ: single-ring, multiple-ring, or non-ring. Whether a given multiple-ring system embodies an open or closed module/ acquisition geometry depends on the arrangement of its constituent module rings.

Figure 18:
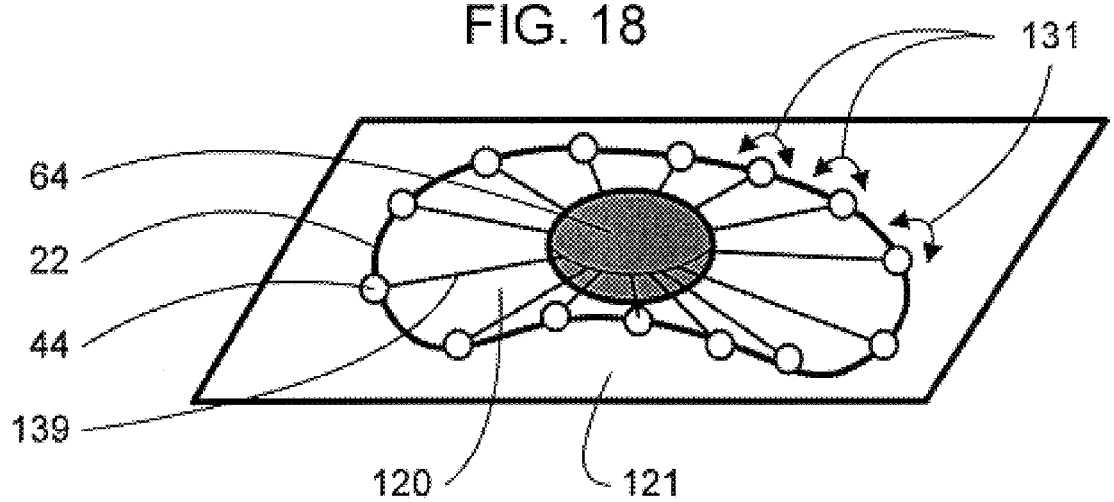
FIG. 18 illustrates the coplanar reconstruction and detector planes of an in-plane acquisition geometry similar to that of conventional SPECT and x-ray CT but with non-orbital detector module motions.

Single-ring embodiments of the disclosed non-orbiting tomographic imaging invention contain one module ring with the geometrical characteristics and the module motion attributes described above. FIGS. 18 and 19 exemplify single-ring embodiments. FIG. 18 shows a single-ring embodiment in which the module plane intersects the object of interest. This geometry, but not the module motion, is similar to that of conventional SPECT and x-ray CT. FIG. 19 shows a single-ring embodiment in which the module plane does not intersect the object of interest or its reconstruction volume. This geometry, but not the module motion, is similar to that of ectomography. In both the intersecting and the non-intersecting single-ring embodiments, the combination of a conventional geometry and the novel non-orbital module motion described below result in a novel embodiment for tomographic imaging.

Multiple-ring embodiments of the disclosed non-orbiting tomographic imaging systems contain more than one like or dissimilar module rings each with the geometrical characteristics and the module motion attributes described above. Dissimilar module rings may have different shapes or characteristic dimensions. The module rings may be distributed axially (placed side by side) in parallel module planes. Such module rings may (as in the non-orbiting breast tomography preferred embodiment described below) or may not share a common axis. The module rings may be axially abutted, or they may be axially spaced as long as the tomographic reconstruction is able to tolerate the sampling gaps resulting from such spacings (see sampling discussion in description of motion below, and sinogram discussion in preferred embodiments section). The module rings may also be distributed radially (stacked one inside the other) forming coplanar rings which may or may not be coaxial or non-coplanar rings which may or may not be coaxial. The module rings may be distributed both axially and radially across parallel planes or non-parallel planes. The modules of a multiple-ring embodiment may form a module surface in the shape of the frustum of a cylinder, cone, paraboloid, or any other analytic or non-analytic surface which conforms to a given object of interest, thereby optimizing or improving the tomographic sampling for that object. Such a module surface may be right or oblique with respect to the module plane(s) which define the end(s) of the module surface. The end(s) of a module surface may or may not contain modules. Such module surfaces may have cross sections which are circular (as in the non-orbital breast tomography preferred embodiment described below), elliptical, or which are described by other closed, simply-connected, planar curves.

A planar non-ring module/acquisition geometry consists of a set of detector modules that lie on a curve that is not closed but otherwise satisfies the definition of a planar module ring (above). Examples of such a geometry include a set of modules that lie on and a planar open curve shaped like a spiral. Modules in such a configuration may be positioned so as to view between other modules which may be closer to the object of interest. Single-[non-ring] planar geometries may easily be generalized by those skilled in the art to multiple-[non-ring] planar geometries.

Non-Planar Embodiments

The preceding descriptions of planar embodiments can be extended to non-planar embodiments by generalizing the module ring (closed curve) and non-ring (open curve) (as defined above) to module arrays (as defined above) in which the arrays are rings. Specifically, one skilled in the art can generalize the above descriptions and discussions of the single-ring and multiple-ring planar embodiments to the analogous single-ring and multiple-ring non-planar embodiments. Similarly, one can generalize the single-[non-ring] and multiple-[non-ring] planar embodiments to the analogous single-[non-ring] and multiple-[non-ring] non-planar embodiments. Examples of non-ring, non-planar embodiments include spiral or helical module arrays which lie on and describe module surfaces of various shapes and types. Shell-like geometries such as hemispheres, paraboloids, ellipsoids, hyperboloids and other analytic or non-analytic surfaces may also be arranged as non-planar module arrays. These examples and descriptions are not intended to limit the scope of the non-planar embodiments of this invention.

Reconfigurable Module/Acquisition Geometries

The shape of the module ring in a single-ring embodiment, or the shape of the module surface described by the modules of a multiple-ring embodiment may be static (fixed) or dynamic (variable) during the acquisition. In a static (fixed) configuration, the modules are mounted on and fixed to a rigid support structure which cannot change shape. In such an embodiment the modules may execute their motion sequences as described below, but such motions do not include motions that would change the shape of the module ring or the module surface during the acquisition. In a dynamic (variable) configuration, the modules are mounted on a support structure which permits passive or active changes in its shape. Passive changes to the shape may be made by a user who manually reconfigures an embodiment designed for such a reconfiguration. Active changes are those made as a result of a drive mechanism provided with the embodiment for this purpose. By either means, the modules are caused to move from one geometric configuration to another thereby changing the shape of the module ring or the module surface. Active or passive changes in configuration may be executed between data acquisition intervals. Active changes may be made during a given data acquisition interval. Such active configuration changes may be executed sequentially with or simultaneous to the tilting, swiveling, rotational, or transnational module motion sequences described below. An example of a dynamic, multi-ring embodiment is one in which the module columns (axially adjacent and aligned modules of a right circular cylindrical module surface) move symmetrically inward at one end forming, for example, the frustum of a right circular cone or paraboloid. The embodiment in this example can thus be reconfigured from a cylindrical geometry, which is suited to imaging a human arm or leg or small animal, to the conical or paraboloidal geometry, which is better suited to breast imaging. The examples and descriptions given here are not intended to limit the scope of the reconfigureability of this invention. One skilled in the art can extend this reconfigureability to planar and non-planar single and multiple non-ring or array geometries. One skilled in the art can make other generalizations resulting in initial, intermediate and final module/acquisition geometries which would be suitable for various other objects of interest.

Detector Module Spacing, Collimation and Motion

The various embodiments of the non-orbiting tomographic imaging invention disclosed here generally have several attributes in common pertaining to detector spacing, collimation, and motion.

Detector Module Spacing and Positioning

The modules in any given embodiment are positioned so that each views the reconstruction volume as much as possible during the acquisition. The spacing of the modules within the set of modules comprising each of the various embodiments may be, but need not be, regular or periodic. It is more important to know the location and viewing direction of the modules with respect to each other and with respect to the object of interest, as provided by the means to determine such information, during the acquisition than it is to arrange the modules in a regular or precise manner. Whatever the type of module/acquisition geometry, the spacing and positioning of the modules comprising the module rings or arrays as well as the module motions are constrained by image quality and other requirements. Chief among these are that the tomographic reconstruction algorithm used produces sufficiently artifact-free images from data acquired by the modules in a given module/acquisition geometry. Design tradeoffs among the reconstructed resolution, sensitivity and lesion contrast also constrain the module locations, orientations and motions.

Detector Module Collimation

The collimators used in a given embodiment may employ a collimation geometry which is:

1) parallel, 2) fixed-focus or variable-focus diverging, 3) one-dimensional or two-dimensional diverging, 4) fixed-focus or variable-focus converging, 5) one-dimensional or two-dimensional converging, or the embodiment may employ a combination of such collimation geometries.

Detector Module Motion

Module motion is a critical aspect of the non-orbital tomography invention. It is convenient to describe and define the detector module motions in terms of two independent coordinate systems. One shall be fixed with respect to the object of interest or the reconstruction volume and shall be called the object-fixed or reconstruction-volume-fixed coordinate system. The other shall be fixed with respect to the detector module (as defined above) and shall be called the module-fixed coordinate system. (Because the detector module is defined to include the radiation detector and the associated collimator, each of which may be caused to move independently with respect to each other and the object of interest, the module-fixed coordinate system shall refer to one or more coordinate systems as follows depending on which component(s) of the detector module undergoes the motion with respect to the object of interest: 1) one coordinate system fixed with respect to the radiation detector, 2) one coordinate system fixed with respect to the collimator, or 3) two coordinate systems, one fixed with respect to the radiation detector and one fixed with respect to the collimator.) The choice of location of the coordinate systems and with respect to a given object is arbitrary. Those skilled in the art typically make such determinations based on convenience in one or more aspects of a given embodiment, such as mathematical description, computation, reconstruction or processing, system architecture, illustration, mechanical design, implementation, cost or other relevant aspects.

For the purpose of describing and defining the detector module motions, we assume that the detector module (its relevant moving component(s)) occupies a volume described geometrically by a rectangular solid. We assume that the face of the detector module (the side(s) of the detector module component(s) which must generally face the object of interest) is flat and is parallel to one of the sides of the rectangular solid. We further assume that the module-fixed coordinate system 1) originates at the geometric center of the solid, and 2) is oriented such that the coordinate axes intersect the faces of the rectangular solid at right angles. (Those skilled in the art recognize that other choices are possible and that the illustrative assumptions made here do not restrict the generality of the description and definition of the detector module motions.) Under these assumptions, one of the coordinate axes is normal to the face of detector module. This normal indicates the nominal direction of view of the module. Specifics of the directions of the collimated projection rays to various points on the radiation detector depend on the collimation geometry. Such collimation geometry may be, and typically is, described and defined with respect to the normal to the detector module.

In general, six quantities are required to define the location and orientation of the detector module. These are the three coordinates which specify the location of the origin of the module-fixed coordinate system with respect to the object-fixed coordinate system, and the three independent angles (Euler angles) which give the orientation of the module-fixed system with respect to the object-fixed system. A tomographic imaging system is capable of complete tomographic sampling of an object of interest it if is capable of viewing all points in the object from all directions. In general, independent variations of all six module position and orientation coordinates are required to generate a module motion which is capable of complete sampling.

Good approximations to tomographically complete sampling, such as those achieved with any realizable tomographic imaging system which is well designed, are sufficient to produce perceptibly artifact-free tomographic reconstructions. The invention disclosed here includes the means of generating such approximately complete sampling. A given embodiment (including module/acquisition geometry, collimation and motion) must tend to maximize the completeness of the sampling obtained from a given number of modules. For a given module/acquisition geometry and a given collimation design, the motion sequence for each module must be chosen so that the direction of view (sampling) of the module passes through (samples) as many points within the object of interest from as many directions as possible. Sinogram simulations of the sampling associated with a given embodiment, described in Detailed Description of the Preferred Embodiments, are typically used by those skilled in the art to help determine if the sampling is sufficient to achieve perceptibly artifact-free image reconstructions.

In the invention disclosed here we use a plurality of detector modules distributed according to one or more of the module/acquisition geometries described above as a means to reduce the number of degrees of freedom of the motion of each module that are required to achieve sufficiently complete tomographic sampling of an object of interest. In some embodiments, such a the non-orbital breast tomography preferred embodiment, only one degree of freedom of motion is required. Usually, such embodiments have a symmetry in their module/acquisition geometry which can be exploited to simplify the motion required to achieve adequate sampling. Some other embodiments, such as the non-orbital cardiac tomography preferred embodiment, will generally not have such simplifying symmetries. They would therefor tend to require more (two, in this case of the cardiac preferred embodiment) independent degrees of freedom of motion of the module viewing direction.

The scope of the invention disclosed here includes motions resulting from independent variations of any one or more of the six quantities defined above excluding 1) motions which result in orbital motion of the module or collimator around the object of interest in the manner characteristic of conventional SPECT or x-ray CT, and 2) those which do not tend to increase the completeness of tomographic sampling. The kinds of motions included in the scope of the invention are: 1) tilting, swiveling, spinning or rotating module motions that result from independent variations of one or more of the module orientation angles (Euler angles); 2) translating or shifting module motions that result from independent variations of one or more of the module location coordinates; or 3) combinations of such tilting, swiveling, spinning, rotating, translating or shifting module motions. For the purposes of describing and defining the motion of the invention disclosed here, the terms tilting, swiveling, spinning or rotating shall refer to variations of the Euler angles described above. Likewise, the terms translating or shifting shall refer to variations of the module location coordinates as described above.

The detector or collimator "wobble" motion characteristic of the Headtome II device is an example of a motion which does not increase the completeness of tomographic sampling. Another such example is the rotation about the normal axis of a detector module with parallel-hole collimation. The geometry and motions of the collimators/detectors in the Headtome II device (reference given in Background of the Invention) do not produce the tomographic sampling required for the embodiments described here. There is a key difference which distinguishes the non-orbital detector systems. The "wobbling" motions characteristic of the Headtome II device are such that the direction of view of any given portion of the collimator is at all times parallel during the wobbling motion. Such wobbling motions are not sufficient to achieve adequate sampling of the object of interest. (Indeed, the wobbling motions of Headtome II were introduced for the purpose of obtaining additional spatial sampling of the fixed intrinsic spatial resolution, which is unrelated to increasing tomographic sampling.) The Head-Tome II collimator must orbit the object in order to achieve adequate tomographic sampling. In the non-orbital tomography embodiments disclosed here the module viewing directions are, in general, not parallel at all times during the module motion, but sweep through the reconstruction volume at various angles. In the invention disclosed here, the collimators need not orbit the object to produce tomographic projection data The location and direction of view of the modules is varied by one of, or by a combination of, two general means. In one means, the direction of view of one or more modules is varied, each as a radiation-detector/collimator unit, by tilting, swiveling, rotating or translating (as described above) the module, or by executing sequential or simultaneous combinations of such motions. In the other means, the direction of view of one or more modules is varied by tilting, swiveling, rotating or translating (as described above) the collimator with respect to its associated radiation detector, or by executing sequential or simultaneous combinations of such motions. The motions of each of the modules in the invention may be independent of the motions of other modules, may be synchronized to the motions of other modules, or may occur in combinations of independent and synchronized motions of modules. Of particular interest for the preferred embodiments described below are tilting, swiveling, rotating and translating motions (as decried above) which are oscillatory (back and forth) or are of limited range. Such motions increase the completeness of sampling of the object of interest by otherwise stationary modules and without requiring orbital motion. The means of achieving adequate sampling does not require that the modules or collimators orbit the object of interest.

Data Acquisition and Control

A means is also provided to communicate to the acquisition subsystem various non-photon information and to synchronize such information with the photon event data. Non-photon information may include status or control data, or status or control signals associated with the patient or various parts of the system. Such data or signals may include:

1) user-entered commands or data used to control one or more aspects of the system (such as acquisition, motion or processing) or to synchronize such control information to the event data;

2) motion subsystem information (such as module position or viewing direction information, or changes in such information) used to relay data or signals to the acquisition or processing subsystems, or to synchronize the motion to the event data, or to synchronize motion in one part of the system to that in another part of the system;

3) patient physiological information such as electrocardiograph signals used to control and synchronize the acquisition, motion or processing of event data in gated cardiac imaging protocols (pertinent to the cardiac tomography embodiment);

4) time markers used, for example, to record the passage of time in the event stream or to synchronize the acquired data to a time reference or to control the temporal aspects of any given acquisition protocol (such as start time, stop time, acquisition duration);

5) any other status or error information originating from any of the subsystems and used for control, acquisition, motion, processing, or reconstruction; or 6) any combination of the above data or signals.

The examples and descriptions given here are not intended to limit the scope of the data acquisition or control. The data acquisition and control means includes the acquisition and utilization of any information that may be required to allow three-dimensional or four-dimensional (including time) tomographic image reconstruction of the object of interest in various clinical and non-clinical applications.

Tomographic Reconstruction

In order to precisely reconstruct an image of an object of interest on a plane through the object, all points on the plane and within the object must be sampled from all directions within the plane. Such an in-plane acquisition geometry is illustrated in FIG. 18. This is a planar single-ring embodiment in which the module plane 121 coincides with the image reconstruction plane 120. The normals 139 to the detector modules 44, which indicate the general directions of view, lie in or are parallel to the reconstruction plane 120 and point at or near the object of interest 64.

When the projection data is incomplete, tomographic reconstruction may be compromised and the image may be degraded. Projections can be incomplete either because there are missing angles in the projection set within the plane or because the projections are obtained out of the plane of reconstruction. The maximum likelihood estimation (MLE) algorithm has been found to be capable of producing satisfactory reconstructions despite the loss of data in the periphery of the reconstruction volume [see for example; D. -C. Yu, W. Chang and T. -S. Pan, "A Study of Reconstruction Accuracy for a Cardiac SPECT system with Multi-Segmental Collimation," *IEEE Transactions on Nuclear Science* 44 (3), 1403–1408 (1997)]. The sampling and reconstruction concepts described above for single-ring embodiments apply to multiple-ring embodiments, such as the non-orbiting breast tomography embodiment, with the appropriate generalizations. They also generalize to non-ring and non-planar embodiments.

A single-ring embodiment in which the module plane does not intersect the object of interest is shown in FIG. 19. In this embodiment, the normal 139 to (the nominal viewing direction of) each module 44 no longer lies in the module plane 121 but deviates from it to point toward the reconstruction volume 140. The modules 44 are mounted and driven so as to sweep their normals 139 (directions of view) through the reconstruction volume 140 by executing the tilting, swiveling, rotating, translating motions in the manner described above. Because the acquisition geometry of this embodiment is not suitable for conventional backprojection reconstruction, ectomographic or MLE reconstruction techniques must be used. Such techniques have been successfully applied to acquisition geometries similar to that shown in FIG. 19. These sampling and reconstruction concepts also generalize to similar multiple-ring embodiments with planar or non-planar module rings.

FIG. 20 illustrates an embodiment of a single-array non-planar module/acquisition geometry described above. This embodiment is a special case of a multiple-array non-planar module/acquisition geometry specialized to a single, non-planar array which is a ring 132. It is also a generalization of the planar single-ring out-of-plane embodiment of FIG. 19 in which the module ring 132 lies on a non-planar manifold 138 rather than a flat plane. This embodiment is well suited for non-orbital cardiac tomography applications and is the basis for the cardiac preferred embodiment described below. In such an embodiment the manifold 138 and the object of interest 137 are the patient's chest surface and heart, respectively. In such an embodiment the ring 132 of modules may be placed in a harness 134 and worn by the patient 136 over the patient's cardiac region. The harness 134 may be of flexible construction so that it conforms to the chest of a variety of patients 136. Alternatively, the harness 134 may be rigid but shaped so as to fit over and around the patient's cardiac region. By either means, the imaging distance between each module 44 and the heart 137 is reduced or minimized, thereby improving or optimizing image quality. The modules 44 are mounted and are driven so as to sweep their normals 139 (directions of view) through the reconstruction volume 140 by executing the tilt, swivel, rotation and translation motions in the manner described above. MLE or other iterative tomographic reconstruction techniques are required to reconstruct the object of interest 137.

DETAILED DESCRIPTION OF THE PREFERRED EMBODIMENTS

Here we disclose two distinct preferred embodiments of the non-orbital tomography invention for use in gamma ray or x-ray imaging: one for non-orbital breast tomography and one for non-orbital cardiac tomography. Each is a special case of one or more of the novel embodiments described in above.

Details Common To Both Preferred Embodiments

Though the two preferred embodiments disclosed here are distinct and serve different applications, they nonetheless share several attributes. We discuss first the common aspects, then we describe each preferred embodiment in detail.

Each of the preferred embodiments disclosed here is composed of a plurality of detector modules configured in one of the module/acquisition geometries described above. Each detector module consists of a photon-sensitive radiation detector 24 and an associated collimator 42, 58 in a housing 59 with radiation shielding. The collimator 42, 58 may be removed for testing or calibration purposes, or it may be exchanged with a collimator 42, 58 having different collimation properties in order to tailor the imaging performance to a particular application. In each preferred embodiment of the non-orbiting tomography invention, neither the modules 44, 88 nor their mounting fixtures 25, 60 orbits the patient or object of interest 64, 137 during the acquisition of projection data In the preferred embodiments disclosed here, each radiation detector 24 is a solid state detector with CZT or CdTe as its photon-sensitive material. Such detectors 24 are approximately several centimeters in length and width and are physically pixelated to form an array of many distinct pixels measuring approximately 1 mm to 3 mm on each side. The photon-sensitive portion adjacent to the surface 23 of these detectors 24 may have a thickness of approximately 4 mm to 15 mm.

The pixels themselves constitute the means of localizing the event (the photon/detector interaction produced by a an incident photon) to a given location within the radiation detector array. The location of such an event is simply the location of the pixel which detected the event. The pixels (that is, the photon-sensitive material from which the pixels are made) are coupled to pulse-processing and readout electronics. Ideally, such electronics reside in an ASIC (application-specific integrated circuit) electrically attached to, or in close proximity to, the detector pixels. The photo-sensitive detector material converts the energy of the incident photon to an electrical pulse from which the photon energy is derived by techniques which are well known in the field of nuclear spectroscopy. The ASIC electronics have one independent channel of analog pulse processing for each pixel. Each channel is event triggered and contains a low-noise preamplifier, pulse shaper, amplifier, peak-and-hold circuitry. The ASIC also provides selectable gain, threshold, shaping time, hold time and readout delay within the hold window. These parameters are judiciously varied to achieve optimum performance for a given photon energy range and event rate. The ASIC electronics generate energy and position information as well as an event trigger for each gamma event. Common to all pixels served by the ASIC is a control logic block and a buffered multiplexed readout. Such control and readout circuitry provides the means to control the ASIC and to output the photon event data.

Figure 11:
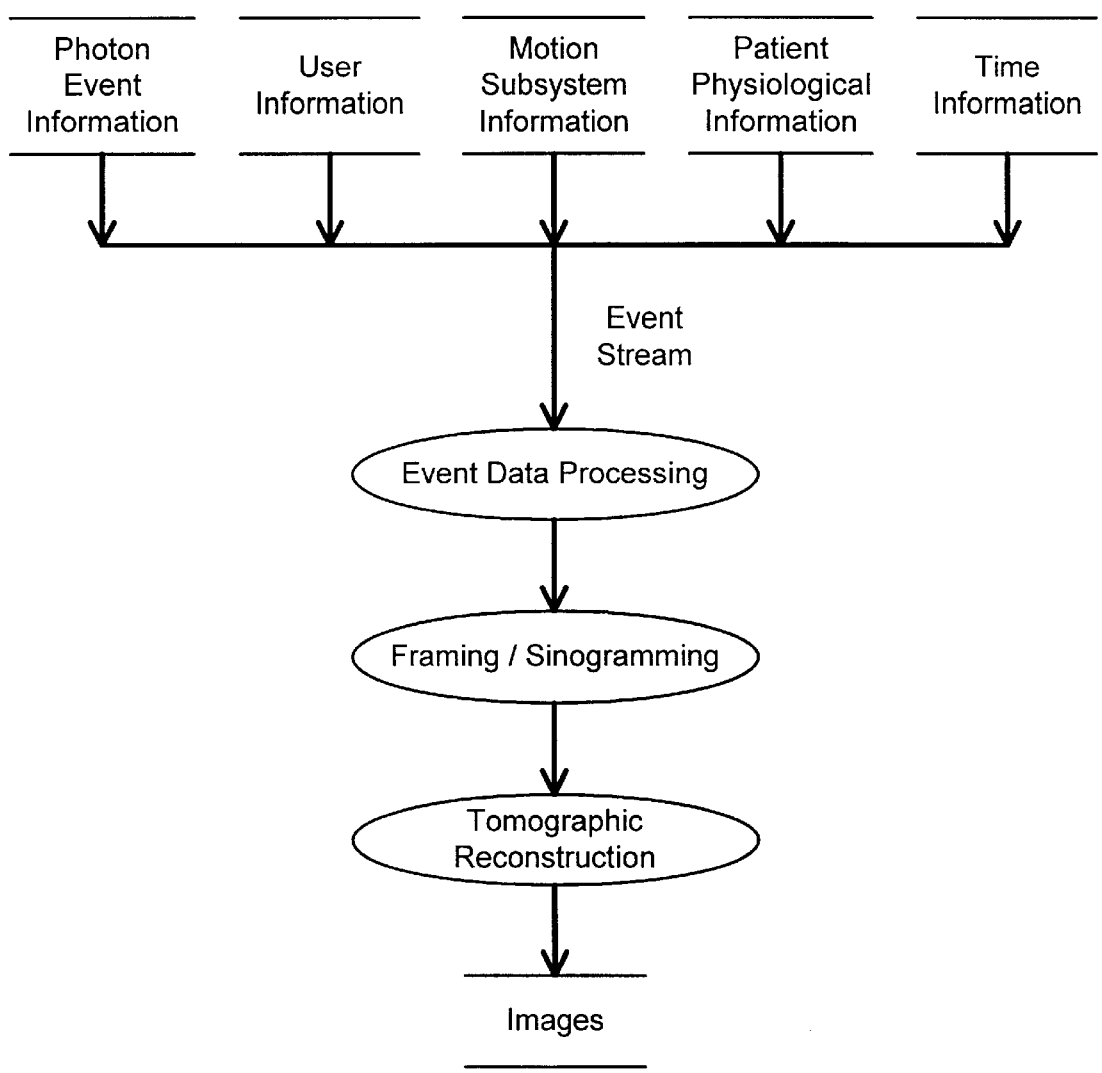
FIG. 11 is a block diagram illustrating the event stream and the data sources which feed it, and the data collection, image processing and reconstruction associated with producing a tomographic image. Control flow and feedback loops are not shown.

A stream of photon event and position data is thus produced by the detectors. The photon event data which must be supplied by the detector system consists of 1) information identifying which module and which pixel within the module detected the event and 2) the digital or analog energy of (or the energy range containing the energy of) the photon event. A means is also provided to integrate into the photon event stream various non-photon information, and to synchronize such information with the photon event data (FIG. 11). This information includes status or control data, or status or control signals as defined and described in the Detailed Description of the Invention. The integrated and synchronized stream of photon and non-photon information associated with the acquisition is sent via a data bus, or by a similar communication means, to a computer. For the purpose of describing the preferred embodiments, the term computer shall refer to 1) the means of acquiring the photon or non-photon data, 2) the means of controlling the acquisition or motion, 3) the means of processing the data, 4) the means of displaying the processed data, or 5) any combination of these means. The format of the data within the stream constitutes the means by which the computer can identify and distinguish the various types of photon and non-photon information.

The computer serves as host for the acquisition system. The acquisition system provides the means, if necessary, to digitize the analog signals so that they can be stored and processed in a digital computer. Performing digitization (analog-to-digital conversion) is necessary at the computer if, for example, it was not done at the detector. The acquisition computer also provides a means of controlling the acquisition of data from the system and coordinating the acquisition with the motions of the modules. Acquisition modes can consist of:

1) reading out the module position and orientation information intermittently or periodically over many photon events as the modules undergo their programmed motion sequences,
2) obtaining the module position and orientation (viewing direction) information with the photon event information for each photon event as the detectors execute their programmed motion sequences,
3) advancing the modules' positions and orientations to the next desired location and orientation, reading out the actual detector positions and orientations, and acquiring a set of photon data for a given duration or a desired number of counts before advancing to the next desired locations and orientations and repeating the acquisition, or
4) a combination of these acquisition modes.

One or more of these acquisition modes may be used in performing various clinical or non-clinical acquisition protocols. In the acquisition subsystem the data from each photon event is synchronized (correlated) with the appropriate module position and orientation readouts. The acquisition subsystem provides a means of performing any event processing computations, including reformatting, calibrations or corrections, which may need to be applied to the data in the stream before reconstruction-related processing.

The computer also hosts the motion control system. The motion control means sends commands to the appropriate drivers to advance the corresponding stepping motors a predetermined amount along a sequence of programmed module locations and orientations which define the desired module motion sequence. A supervisory control means coordinates motion control, module position and orientation measurement and data acquisition to execute an imaging acquisition sequence (protocol) according to one of the acquisition modes describe above. Upon completion of the acquisition sequence, or in parallel with the acquisition sequence, the data is processed by reconstruction means to create the tomographic image. The computer which hosts the acquisition control and motion control can also perform the image reconstruction and any post-reconstruction processing that may be required. Post-reconstruction processing, analysis and viewing of the tomographic images can take place locally on the processing computer or remotely on another computer.

Preferred Embodiment For Non-Orbiting Breast Tomography

Figure 14:
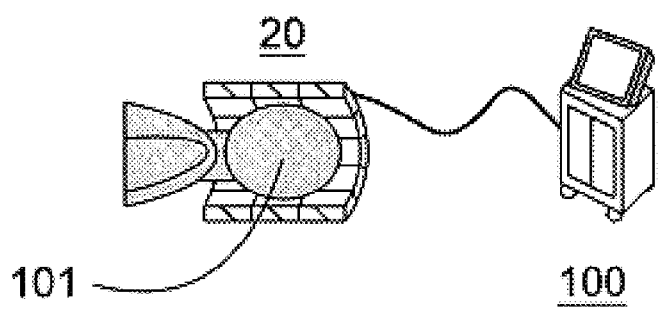
FIG. 14 shows a schematic cut-away drawing of the disclosed non-orbital tomography invention in brain imaging configuration.
Figure 15:
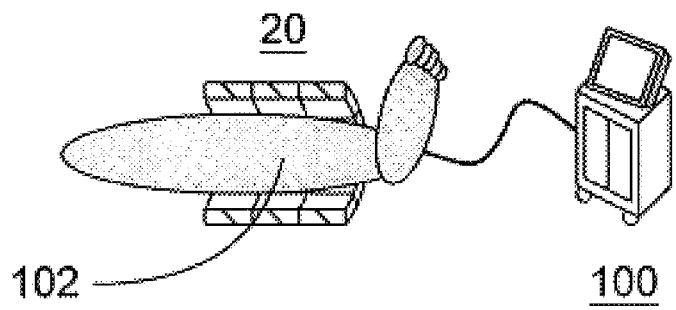
FIG. 15 shows a schematic cut-away drawing of the disclosed non-orbital tomography invention in human limb imaging configuration.
Figure 16:
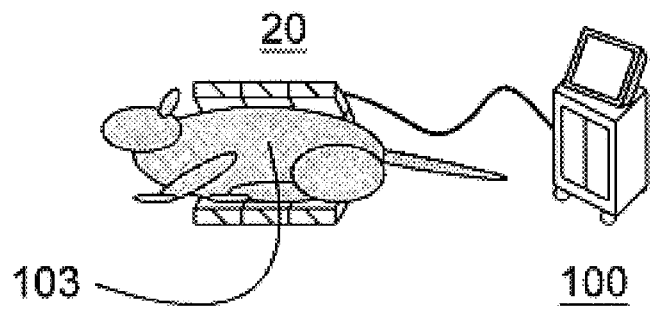
FIG. 16 shows a schematic cut-away drawing of the disclosed non-orbital tomography invention in small animal imaging configuration.

The first non-orbital tomography preferred embodiment is a device 20 intended for tomographic Nuclear Medicine studies of the breast (see FIG. 1). With relatively minor parametric adjustments, this preferred embodiment may also be used for tomography of the human head 101, human limbs 102 (arms or legs), or small animals 103 as indicated in FIGS. 14–16 or of other objects of similar size and shape. The most obvious difference between the breast and cardiac preferred embodiments, FIGS. 1 and 20, respectively, is the module/acquisition geometry. The module motion is also different, as will be described below.

The module/acquisition geometry of this preferred embodiment, illustrated in the sectional view of FIG. 1, is a special case of the class of multi-ring, planar embodiments (described and defined above). This preferred embodiment consists of an axially abutted stack of three, planar, nine-module rings 22. Each ring 22 is circular and coaxial. The module rings 22 are parallel, and the module surface 21 thus formed is a right circular cylinder as illustrated in the top down view of FIG. 2. The radius 28 of each ring 22 is approximately 6–8 cm depending on the azimuthal spacing 30 between adjacent modules 44. The spacing 30 between modules 44 is uniform and is determined by the size of the collimated modules 44 and the range of transverse swiveling motion required for adequate sampling of the reconstruction volume 63. Such design information is readily determined using computer simulation of the sinogram sampling patterns (described below). The module assembly 26 for the module 44 may drive a single module 44 as shown in FIGS. 3–6 or may be extended to drive a plurality of modules 44, such as the 3-module column 27, operating as a detector unit 27 as shown in FIG. 1. Each set of three axially adjacent modules 44 defines such a module column 27 for this embodiment. The module rings 22 are aligned such that each module column 27 is parallel to the axis of the device 20. The module rings 22 form nine such columns 27 of three-detector modules 44. Only five columns 27 of the nine columns 27 are shown in FIGS. 1 and 14–16, and only one column 27 of the nine columns 27 is fully illustrated in FIGS. 1 and 2. However, actuation means 36, 38 is provided for each of the nine columns 27.

The disclosed non-orbital breast tomography preferred embodiment 20 requires only one degree of freedom in the motion of its detector modules 44 to achieve adequate tomographic sampling. The version of the preferred embodiment described below employs a detector module 44 which is moved by means of a geared assembly 36 which causes a one-dimensional swiveling motion of the module 44. Such a means is one of many possible means which can be devised by one skilled in the art to achieve the motions required for adequate tomographic sampling and shall not limit the scope of the invention.

The module assembly 26 provides structural support for the module 44 and its electronics, photon shielding, and electromagnetic interference shielding. The module assembly 26 also provides a means 41 to mechanically attach the collimator 42 to the photon-sensitive radiation detector medium 24. The collimator 42 is attached by conventional means which allow the collimator 42 to be exchanged or removed for calibration and testing purposes. The module assembly 26 also provides a means to attach the module 44, whether collimated or uncollimated, to the mounting fixture 25 that varies the position or direction of view of the modules 44. Such a mounting fixture 25, shown in FIGS. 1 and 2, consists of a small stepping motor 38 driving a geared assembly 36. The geared assembly 36 produces a change in direction of the view of the module 44 by causing it to swivel back and forth in a transverse plane (perpendicular to the axis of the module rings 22) about a central or radial viewing direction.

Each module column 27 swivels along a central axis 32 which is aligned with central shaft 33. The radiation detector 24 and collimator 42 of each module 44 in the column 27 move together as a unit. The viewing directions of the modules 44 within each column 27 are aligned so that their directions of view are parallel and coplanar. The mounting fixture 25 (transverse drive mechanism), consisting of a geared assembly 36 and a stepping motor 38, causes the central shaft 33 to undergo oscillatory axial rotations which, in turn, cause the module column to execute a transverse swiveling motion 34 through a −60° to +60° arc. Such swiveling sweeps the module viewing direction through a transverse plane perpendicular to the axis of the device 20, as in FIG. 10. A computer 100 (FIG. 14–16) controls the swivel motion 34 through the gear train 36 with a precision gear ratio in forward and reverse increments provided by the stepping motor 38. No other motion is required in this embodiment. However, if a version of the embodiment has axially spaced module rings 22, one would need to add an independent axial component to the module motion in order to tomographically sample across such gaps.

Detector module 44 viewing directions are determined by stepping motor 38 feedback provided by a linear potentiometer 40. A means to sample information from such a position encoder 40 is provided so that the module orientation data can be read out electronically along with the photon event data coming from the detector modules 44 (as shown in FIG. 11). Each radiation detector 24 has a high resolution collimator 42 (FIGS. 1, 2 and 3–7). The basic assembly of the detector module 44 for this embodiment is illustrated in FIG. 3. A half gear 46 is mounted to the back plate 48 of the detector module 44 and the collimator 42 is locked in place on the front radiation sensing surface 23. The back panel 48 has a vertical half round channel 56 centered in its surface which in conjunction with the half gear 46 center hole 47 form the pivot point 49 (or central axis 32) for the detector module swivel motion in this configuration. The module motion employed in this preferred embodiment consists of transverse swiveling 34 of each module 44 through a −60° to +60° arc.

Figure 9:
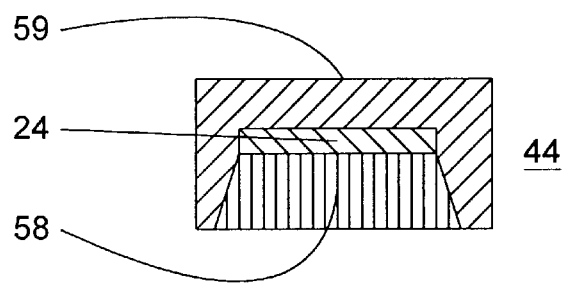
FIG. 9 shows an enlarged portion of FIG. 8, showing a cross section of a collimated detector module with shielding/housing.
Figure 10:
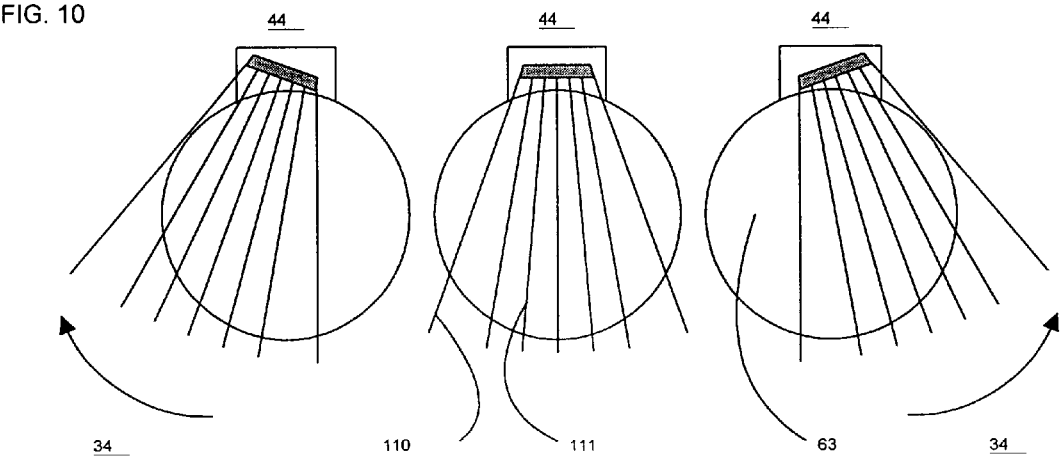
FIG. 10 illustrates the transverse swiveling motion of a detector module and its projection lines from of a detector module from FIGS. 8 and 9 through the reconstruction volume.

The pattern used in all the Figures to indicate a collimator 42 does not represent the actual hole size or septal pattern for the collimator 42, but merely represents what one skilled in the art can identify as a collimator 42. Our embodiments are illustrated in FIGS. 1–7 and 23–25 with high-resolution parallel-hole collimator(s) 42. As an alternative to parallel-hole collimation, diverging collimation 58 may also be used as shown in FIGS. 7 and 9–10. The diverging collimator 58 preferred for the non-orbiting breast tomography embodiment has a collimation geometry which is parallel in the axial direction and is a diverging fan-beam in the transverse direction with a 20° opening angle of view (from −10° to +10°).

Calculations for the non-orbital breast tomography preferred embodiment show that on average the modules 44 will be significantly closer to the breast 64—better than a factor of two closer compared to conventional SPECT systems—resulting in improved spatial resolution for equivalent collimator 42, 58 angular resolution. The close proximity is sufficient to support better than 5 mm three-dimensional spatial resolution over the entire breast 64. This represents a factor of 2 improvement over conventional systems. Accounting for intrinsic resolution contributions, the system sensitivity per unit area of detector 24 will be increased by a factor of approximately 2.8 to 5. In this embodiment, all 27 modules 44 in the system 20, approximately 67 in$^2$, are used to view the breast 64 (or the reconstruction volume 63 which contains the breast 64) from multiple directions to produce a tomographic image. In contrast, conventional gamma camera systems have much larger detector areas (typically about 300 in$^2$), but use only about 22 in$^2$ (less than 10%) of each detector 24 to view the breast 64 at any one time, and can produce only a planar image.

When the module ring 22 is symmetric and the modules 44 are equispaced about the module ring 22, as is the case in this preferred embodiment, the number of modules 44 in the ring 22 is chosen to be odd. This serves as one possible means to "break the symmetry" of the module/acquisition geometry and in order to improve uniformity of tomographic sampling. Under these conditions, each module 44 in the ring 22 is located directly opposite the gap between adjacent modules 44 on the other side of the ring 22. See FIG. 8. Said differently, a module ring diameter that passes through the gap between adjacent modules 44 on one side of the ring 22 passes directly through (or near) a midline of the module 44 on the other side of the ring 22. Thus, each module 44 samples projection data across the gap between adjacent modules 44 on the other side of the ring 22. This increases sampling uniformity throughout the reconstruction volume 63 and improves image quality. The sampling characteristics of the non-orbiting breast tomography embodiment are such that the regions near the axis of the device 20 are sampled uniformly from all directions. However, points closer to the module ring are sampled non-uniformly and from a limited number of angles.

Figure 12:
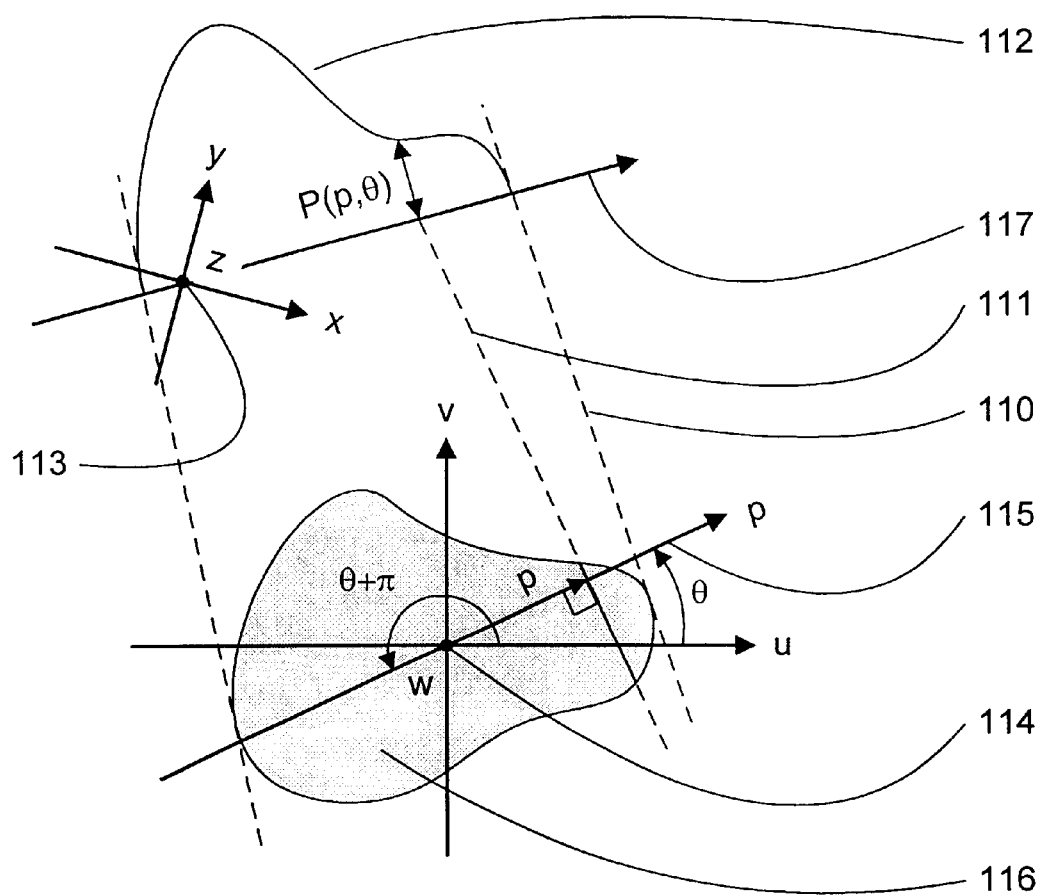
FIG. 12 illustrates the detector and object geometry used to define the sinograms and the projection data.

Sinograms help guide the design of the module geometry and motion for a given non-orbital tomography embodiment. They readily illustrate the completeness of the tomographic sampling of the projection data for the embodiment. Sinograms for the non-orbital breast tomography preferred embodiment are shown in FIG. 13. They are derived from the acquired pixel data using the conventions illustrated in FIG. 12. The projection lines, such as 110 and 111, in FIG. 12 indicate the line of sight from a given detector pixel (not shown) at the detector surface 117 through the collimator (not shown). The planes or surfaces swept out by the various projection lines during the course of module motion define the various planes or surfaces of reconstruction. The axis of rotation of the module is the axis 113 of swivel for simple swivel motions or is the instantaneous axis 113 of module rotation for more complex motions. Each projection line 111 in its plane of reconstruction can be uniquely defined by two coordinates θ and p defined in a object-fixed system of coordinates 114, u,v,w. The angle θ corresponding to a given projection line 111 is the angle of the normal line 115 which 1) passes through the origin of the object-fixed coordinates 114 and 2) is perpendicular to the projection line 111 as shown in FIG. 12. The coordinate p is the displacement of the projection line 111 from the object-fixed origin 114 along the normal 115 to the projection line 111. Each point (θ,p) in the sinogram represents one projection line 111 through the object of interest 116 and along which the projection data P(θ,p) 112 is measured by a single detector pixel. FIG. 13 represents the pixel data from the imaging system of FIG. 1 rebinned into the sinogram coordinates (θ,p). In FIG. 13, each pixel in the system is mapped to two points in the sinogram (θ,p) and (θ+π,−p) which are represented by dots on the sinogram. The values at the two points (θ,p) and (θ+π,−p) would be equivalent in the absence of attenuation. A high density of dots implies that the sinogram is well-sampled in that region, while a low density represents low sampling. In FIG. 13.a, the modules have parallel-hole collimators and the modules swivel from −60° to +60° with good sampling for the entire sinogram. In FIG. 13.b, the modules have diverging collimators with 20° opening angle and the detectors swivel from −60° to +60°. In both configurations the entire field of view has adequate sampling for perceptibly artifact-free reconstructions using existing methods. In the breast tomography preferred embodiment, as in any non-orbital tomography embodiment, the module/acquisition geometry, the module motion and the collimation geometry must work together to produce adequate sinogram sampling. To design the sampling geometry, motion and collimation, one judiciously varies the design parameters in sinogram simulations for the embodiment to achieve acceptable sampling uniformity and density within the reconstruction volume. MLE or other iterative reconstruction techniques are required to tomographically reconstruct the reconstruction volume containing the object of interest.

Preferred Embodiment For Non-Orbiting Cardiac Tomography

The second non-orbital tomography preferred embodiment is a device 130 intended for tomographic Nuclear Medicine cardiac studies (see FIGS. 17 and 20). This embodiment is a special case of the single-array, non-planar module/acquisition geometry in which the module array is a non-planar module ring 132 (FIG. 20). Although not illustrated, this embodiment could include one or more modules 88 inside the module ring 132, making the module ring 132 a module array as defined above. Like the breast tomography embodiment 20 disclosed above, the cardiac tomography preferred embodiment 130 has a geometry which conforms to the region of interest, the chest of the patient 136, in this case. The cardiac tomography embodiment 130 contains a plurality of detector modules 88 which lie in a non-planar module ring 132. The module ring 132 is housed in a harness 134 which is positioned on or worn by the patient 136 on the patient's chest over the patient's cardiac region, as shown in FIG. 17. The chest of the patient 136 defines the non-planar module manifold 138.

Figure 21:
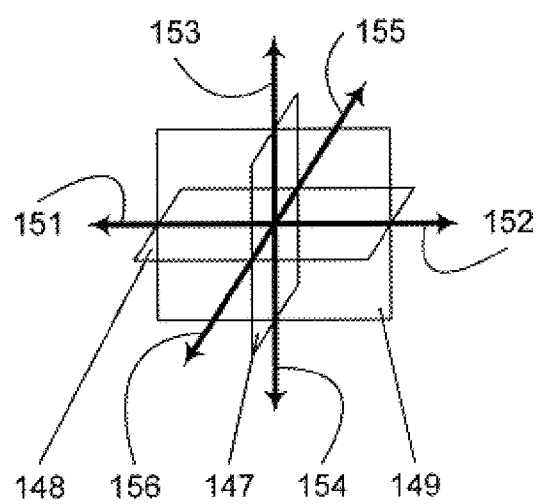
FIG. 21 serves to clarify and illustrate the anatomical directions as well as the sections for the embodiment described in FIG. 20.
Figure 22:
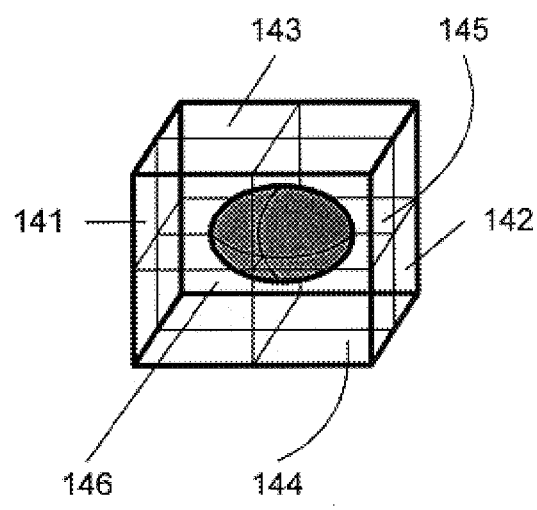
FIG. 22 serves to clarify and illustrate the six surfaces of the reconstruction volume for the embodiment described in FIG. 20.

The module harness 134 is positioned so that the modules 88 in the module ring 132 are able to view all 6 sides of the cardiac reconstruction volume 140, shown for purposes of illustration in FIG. 20 as a cube containing the heart 137. The cube 140 is oriented so that its saggital surfaces 141 and 142, coronal surfaces 143 and 144, and transverse surfaces 145 and 146, are parallel to standard saggital 147, coronal 148, and transverse 149 sections, respectively, through the human body 136. See FIG. 21. Positioning in this manner maximizes the completeness of the sampling achievable from the surface 138 of the chest through the regions of the chest which are closest to the heart 137 and which, therefor, introduce the least amount of attenuation and scatter. Each module 88 views 1,2 or 3 of the 6 visible sides of the cardiac reconstruction volume 140. (For clarity of the illustration, FIG. 20 shows the module ring 132 viewing only 4 of the 6 sides of the cardiac reconstruction volume 140.) The transverse (side-to-side) extent and positioning of the module ring 132 is such that the modules 88 on the medial side 151 view the medial saggital surface 141 and anterior coronal surface 143, while the modules on the left-lateral side 152 of the ring view the left saggital surface 142 and posterior coronal surface 144. The axial (head-to-toe) extent and positioning of the module ring 132 is such that the modules 88 on the superior side 155 view the superior transverse surface 145 in addition to 142 and 143, while the modules on the inferior side 156 of the ring view the inferior transverse surface 146 in addition to 142 and 143. See FIG. 22 for clarification.

The module harness 134 may be flexible, capable of conforming closely to the chest of a given patient 136, or it may be rigid or semi-rigid, capable of approximately conforming to the chest of a given patient 136.

Attenuation and scatter of the emitted radiation by breast tissue is a major source of image degradation in cardiac tomography studies in women. Because of its ring shape, the module harness 134 disclosed here may be worn by female patients 136 on chest surface and around the breast such that no detector module must view through the attenuating breast tissue. The module harness 134 contains 15 modules 88 equally spaced along the module ring 130. The circumference of the harness 134 is approximately 26 inches, and the distance across the module ring 130 measured along the module manifold 138 (analogous to the diameter of a circle) is approximately 8.5 inches. The harness 134 allows for small spacing between modules 88 to permit module motion and harness flexibility. The spacing between modules 88 is adjustable to accommodate a range of patient chest sizes. The module spacing determined by the size of the collimated modules, the range module motions (described below) required for adequate sampling of the heart 137. Such design information is readily determined using computer simulation of the sinogram sampling patterns (as described for the mammography preferred embodiment).

The module assembly 90 provides structural support for the module 88 and its electronics, photon shielding, and electromagnetic interference shielding. The module assembly 90 also provides a means to mechanically attach the high-resolution collimator 42 to the photon-sensitive radiation detector medium 24. The collimator 42 is attached by conventional means 41 which allow the collimator 42 to be exchanged or removed for calibration and testing purposes. The module assembly 90 also provides a means to attach the module 88, whether collimated or uncollimated, to the mounting fixture 60 that varies the position or direction of view of the modules 88.

Unlike the breast tomography preferred embodiment 20 described above, the disclosed non-orbital cardiac tomography preferred embodiment 130 requires two degrees of freedom in the motion of its detector modules 88 to achieve adequate tomographic sampling. The version of the preferred embodiment described below employs a detector module 88 which is moved on a pivot ball 68 by two independent means described below, one for each degree of freedom of motion. Such means are one of many possible means which can be devised by one skilled in the art to achieve the motions required for adequate tomographic sampling and shall not limit the scope of the invention.

In the non-orbiting cardiac tomography preferred embodiment each detector module 88 pivots on the ball end 68 of a hollow shaft 70 (FIGS. 23–25). A cam roller 72 rotates around a flat (or contoured) ring track 74 which swivels and tilts the detector module 88 causing its normals 139 (direction of view) to sweep through cone-like surfaces through the reconstruction volume 140 in a prescribed manner. The radiation detector 24 and high-resolution collimator 42 of each module 88 move together as a unit. The detector modules 88 thereby sample image data at controlled angles. These imaging modules are constructed using a cam roller 72 to create a rotational pivot of the detector module 88 around its center as illustrated in FIGS. 23–25. A drive gear 80 driven by either a linear or stepping motor (not shown) spins a cam gear 82 attached to the assembly 60 rotating the spin disk 84 which contains the cam roller 72. An electronically controlled offset device 86 adds an independent and controlled alteration to the direction of view generated by the cam roller and is used as a means of adding an independent degree of freedom to the motion of the module 88. The offset device 86 effectively varies the opening angle of the cone-like surface swept out by the module direction of view. The combination of the two independent motions constitutes the means of sampling of the reconstruction volume. The spin disk 84 rotates perpendicular to the pivot shaft 70 mounted to a flexible, fixed ring 60 or plate. As the cam roller revolves on the ring track 74 it tips the surface of the track 74 and sweeps the viewing direction 139 of the detector module 88 and each pixel in a circular pattern. The normal ray 139 from the detector module 88, indicating the nominal direction of module view, thus sweeps out a cone-like surface in space. Independently controlled combinations of the resulting module motions are used to sweep the module viewing direction 139 through all regions of the reconstruction volume 140 in such as way as to increase the completeness of the tomographic sampling of the cardiac reconstruction volume 140. Detector module viewing directions are determined by stepping motor (not shown) feedback provided by a linear potentiometers (not shown) for each motion degree of freedom. A means to sample such a position encoders are provided so that the module 88 orientation data can be read out electronically along with the photon event data coming from the detector modules (as shown in FIG. 11). Each radiation detector 24 has a high resolution collimator 42 (FIGS. 23–25). The basic assembly of the detector module 88 for this embodiment is illustrated in FIGS. 23–25. The collimator 42 preferred for the non-orbiting cardiac tomography embodiment has a parallel collimation geometry. Alternatively, a two-dimensional, fixed-focus or variable-focus, diverging collimator 58 may be used on one or more of the modules 88 to increase the completeness of the tomographic sampling.

The tomographic sampling of the reconstruction volume 140 in the non-orbiting cardiac tomography embodiment 130 is determined by 1) the location, orientation and spacing of the modules 88 in the module ring 132, 2) the type of module collimation (parallel 42 or diverging 58), and 3) the design of the module collimation, and 4) the combination of the two independent degrees of freedom of module motion described above. To design the sampling geometry, motion and collimation, one judiciously varies the design parameters in sinogram simulations for the embodiment to achieve acceptable sampling uniformity and density within the reconstruction volume 140 (as described for the breast tomography embodiment). MLE or other iterative reconstruction techniques are required to tomographically reconstruct the reconstruction volume 140 containing the object of interest 137.

The preferred embodiments described above are ones for which only one or two degrees of freedom of motion are required. The non-orbital tomography system invention disclosed here shall not be limited to the designs described here. One skilled in the art may devise means other than those described above to achieve adequate tomographic sampling. The scope of the invention encompasses the combinations of the three independent rotational and the three independent translation degrees of freedom of module or collimator motion which may be required by a specific application to achieve adequate tomographic sampling. The designs described here can be generalized to produce module or collimator motion sequences with up to the 6 degrees of freedom required to describe the motion of each moving component of the system.

Methodology

The patient or object of interest is injected or otherwise laden with a tracer, usually a radioisotope-labeled pharmaceutical, that produces an identification or measure of function or anatomy. The radioisotope decays in situ and produces a stream of ionizing radiation emerging from the body or object of interest in all directions. The object or patient is inserted into the non-orbiting tomographic imaging system or is otherwise brought to close proximity with the system. The area of interest for the study is placed into the active imaging area of the system. For some studies the object or patient will be set up with the system before the tracer is introduced.

Regular calibration of the imaging detectors, the collimated detector modules, and the motion components is performed. These calibration procedures utilize fixtures to distribute point-sources, line-sources or other radioisotope distributions at known positions and orientations within the imaging system. Specialized acquisition protocols or motion sequences are used to generate test and calibration data sets. Specialized processing software is used to analyze the test and calibration data and produce correction and calibration data sets. These data sets are used to produce or update corrections for the collimated or uncollimated detector response, the module or collimator position or orientation information, or the motion control system.

With the object or patient in place, the control computer is used to activate the detectors and the event data stream is recorded. The object of interest or the patient is kept stationary relative to the detector ring during this part of the study. The motion control system begins the pre-programmed detector motions to systematically sample the projection data from the radioisotope distribution. The data acquisition system records and stores the position information for each detector orientation either from the motion control system or from a position readout mechanism. Upon completion of the data acquisition phase of the study the object or patient can be released from the system. The acquisition data is then processed by the processing station of the computer. The projection data, along with pertinent system information (e.g. system corrections, physiological markers, attenuation data, collimation specifications) is taken as input to the reconstruction processor. The processor uses the appropriate algorithm to implement the tomographic reconstruction calculation. The reconstruction process produces tomographic images and stores the results for further processing or viewing.

One application of the methodology is for the tomographic Nuclear Medicine study of the heart. In this application the patient is either given a pharmacologic (e.g. intravenous administration of Adenosine) or a physical (e.g. tread mill) stress on the cardiovascular system. At peak stress a radio-pharmaceutical (e.g. Tc-99m labeled sestamibi or Tl-210 labeled Thallous Chloride) is injected. The patient is then brought to the non-orbiting tomographic imaging system (or the system is brought to the patient). The cardiac version is fitted to the chest wall and attached to the patient with a harness. Alternatively the device is positioned to the chest wall by means of a structure supporting the detector ring. The detector ring is fitted to the chest wall to surround the region of the heart (as described above) while avoiding looking through excessive muscle or other soft tissue (e.g. by following the perimeter of the breast in female patients). The detector ring is thus able to view the heart through a minimal amount of interposing soft tissue. Once the detector ring is positioned, the acquisition computer begins the data acquisition sequence and initiates the motion control program. The projection data is stored in a computer and is available for processing. After a period of rest a second injection can be administered to map the resting state of the heart. Alternatively the radioisotope injected for the stress session can be allowed to redistribute to represent the resting state. The detector ring is again fitted to the chest as before and the imaging procedure repeated. For systems with a harness, the detector system can be left in place to be sure that the rest-stress images are properly aligned. If the harness is not used or if it must be removed, computational procedures can be used to align (register) images based on anatomical or other features in the images. A preferred mode of operation for this procedure is to use one isotope (e.g. Tl-201) for rest and a different isotope (e.g. Tc-99m) for stress. In this case the rest and stress images can be performed in quick series. A further preferred mode of operation is to again use dual isotopes for rest and stress but to image them simultaneously to acquire both the rest and stress image with a single imaging session. Different acquisition windows (ranges of photon energy) are used for each isotope because each isotope has a characteristic energy spectrum.

Cardiac gating can be accomplished by fitting the patient with electrocardiograph electrodes, reading the electrical signals from the heart and feeding that information into the event data stream of the projection data This data is then used to sort the photon events according to the part of the cardiac cycle they occurred in. After tomographic reconstruction or other processing, the images can be viewed in relation to their timing in the cardiac cycle.

Another application of the methodology is for the tomographic Nuclear Medicine study of the breast. In this application the patient is injected with a radio-pharmaceutical (e.g. Tc-99m labeled sestamibi). The patient is then brought to the non-orbiting tomographic imaging system (or the system is brought to the patient). The patient lies prone on a bed with a cut-out through which the breast hangs freely from the patient's chest wall into the imaging volume of the imaging system. This imaging configuration is ideally suited to breast imaging because it images the breast from all sides. Moreover, it presents a low solid angle (range of acceptance angles) from the detector to the chest muscle, heart or other interior regions of the chest, three sources of background and scatter radiation which can degrade image quality. The system is brought from below and fitted around the breast and to the chest. The device is positioned by means of a structure supporting the detector system. Once the detector system is positioned, the acquisition computer begins the data acquisition sequence and initiates the motion control program. The projection data is stored in a computer and is available for tomographic reconstruction and other processing.

Another application of the methodology is for the tomographic Nuclear Medicine study of the brain. In this application the patient is injected with a radio-pharmaceutical. The patient is then brought to the non-orbiting tomographic imaging system (or the system is brought to the patient). The patient lies preferably supine on a bed. The non-orbiting tomographic system device is positioned by means of a structure supporting the detector system so that the central axis of the imaging system is parallel or nearly parallel to the long axis of the patient. The head is inserted into the imaging area of the system. The head can be supported by an inner supporting structure within the imaging system. Once the detector zing and patient are positioned, the acquisition computer begins the data acquisition sequence and initiates the motion control program. The projection data is stored in a computer and is available for tomographic reconstruction and other processing.

Another application of the methodology is for the tomographic Nuclear Medicine study of a limb (leg or arm). In this application the patient is injected with a radio-pharmaceutical. The patient is then brought to the non-orbiting tomographic imaging system (or the system is brought to the patient). The patient lies either supine or prone on a bed. The non-orbiting tomographic system device is positioned by means of a structure supporting the detector ring so that the central axis of the imaging system is parallel or nearly parallel to the long axis of the limb. The limb is inserted into the imaging area of the system. The limb can be supported by an inner supporting structure within the imaging system. Once the detector ring and patient are positioned, the acquisition computer begins the data acquisition sequence and initiates the motion control program. The projection data is stored in a computer and is available for tomographic reconstruction and other processing.

Another application of the methodology is for the tomographic Nuclear Medicine study of a small animal such as a dog. In this application the animal is injected with a radio-pharmaceutical. The animal is then sedated and/or restrained and brought to the non-orbiting tomographic imaging system (or the system is brought to the animal). The animal lies on a bed or pallet. The non-orbiting tomographic system device is positioned by means of a structure supporting the detector ring so that the central axis of the imaging system is parallel or nearly parallel to the long axis of the animal. The animal is inserted into the imaging area of the system. The animal can be supported by an inner supporting structure within the imaging system. Once the detector ring and animal are positioned, the acquisition computer begins the data acquisition sequence and initiates the motion control program. The projection data is stored in a computer and is available for tomographic reconstruction and other processing.

Another application of the methodology is for the tomographic study of a radioactive object (e.g. a drilled oil well core). The object is then brought to the non-orbiting tomographic imaging system (or the system is brought to the object). The non-orbiting tomographic system device is positioned by means of a structure supporting the detector ring so that the central axis of the imaging system is parallel or nearly parallel to an axis of the object. The object is inserted into the imaging area of the system. The object can be supported by an inner supporting structure within the imaging system. Once the detector ring and object are positioned, the acquisition computer begins the data acquisition sequence and initiates the motion control program. The projection data is stored in a computer and is available for tomographic reconstruction and other processing.

The applications presented here are representative of the range of applications of the invention. One skilled in the art can define additional applications. The methods of application of this device is not limited by the specific applications detailed here.

What is claimed is:

1. An imaging system for acquisition of tomographic emission data from a radiation source, the imaging system comprising: a plurality of detector modules, module positioning means, and means for acquiring data, wherein
   each detector module comprises a radiation detector and a collimator,
   the module positioning means providing means for adjusting the position and viewing angle of each detector module so that each detector module has the ability to view the radiation source from a plurality of positions and angular directions and the ability to move independently of other detector modules, and
   wherein data comprises radiation emission data and information regarding the position and orientation of each detector module,
   wherein during acquisition of tomographic emission data each detector module moves independently, sweeping through said plurality of positions and angular directions so as to optimize data acquisition without orbiting said radiation source.

2. The imaging system of claim 1 wherein the position and orientation of the detector modules can be varied by single axis rotational motions.

3. The imaging system of claim 1 wherein the position and orientation of the detector modules can be varied by means of multi-axis rotational motions.

4. The imaging system of claim 1 wherein the position and orientation of the detector modules can be varied by means of translational motions.

5. The imaging system of claim 1 wherein the position and orientation of the detector modules can be varied by means of a combination of multi-axis rotational motions and translational motions.

6. The imaging system of claim 5 wherein said multi-axis rotational motions and translational motions are oscillatory.

7. The imaging system of claim 5 wherein the module positioning means comprises a mechanism which is attached to the detector module and is driven by an actuating means, wherein the actuating means comprises an electro-mechanical motor.

8. The imaging system of claim 5 wherein the module positioning means comprises a mechanism which is attached to the detector module and is driven by an actuating means, wherein the actuating means comprises a hydro-mechanical motor.

9. The imaging system of claim 5 wherein the module positioning means comprises a mechanism which is attached to the detector module and is driven by an actuating means, wherein the actuating means comprises a pneumatic device.

10. The imaging system of claim 5 wherein the module positioning means comprises a mechanism which is attached to the detector module and is driven by an actuating means, wherein the actuating means comprises a combination of an electro-mechanical motor, hydro-mechanical motor, and pneumatic device.

11. The imaging system of claim 10 where the mechanism is connected to a position measuring and recording means which determines the position and orientation of the detector module.

12. The imaging system of claim 11 where the position measuring and recording means is comprised of a mechanical device.

13. The imaging system of claim 11 where the position measuring and recording means is comprised of an electrical device.

14. The imaging system of claim 11 where the position measuring and recording means is comprised of optical devices.

15. The imaging system of claim 11 where the position measuring and recording means is comprised of an electro-mechanical device.

16. The imaging system of claim 11 where the position measuring and recording means is comprised of an electro-optical device.

17. The imaging system of claim 11 where the position measuring and recording means is comprised of a combination of mechanical, electrical, optical, electro-mechanical, and electro-optical devices.

18. The imaging system of claim 1 where the detector module further comprises a detection surface and a photon event location recording means, said photon event location means providing the determination of the location of the interaction of a photon on the detection surface of the radiation detector.

19. The imaging system of claim 1 where the radiation detector is comprised of a scintillator and photomultiplier tubes.

20. The imaging system of claim 1 where the radiation detector is a solid state detector.

21. The imaging system of claim 20 where the solid state detector is comprised of Cadmium Telluride as a radiation interaction and conversion medium.

22. The imaging system of claim 20 where the solid state detector is comprised of Cadmium Zinc Telluride as a radiation interaction and conversion medium.

23. The imaging system of claim 1 where means are provided which enable the collimator to change position or orientation relative to the radiation detector.

24. The imaging system of claim 1 wherein the positioning means is maintained in space using a mounting means.

25. The imaging system of claim 24 wherein the mounting means is rigid.

26. The imaging system of claim 24 wherein the mounting means is flexible.

27. The imaging system of claim 24 wherein the mounting means enables rearrangment of the plurality of detector modules during use.

28. An imaging system for acquisition of tomographic imaging information from a radiation emission source, the imaging system comprising radiation detection means, positioning means, information management means, and a radiation emission source wherein said radiation detection means comprises a plurality of detector modules, each of said detector modules comprising a radiation detector, a collimator, and a photon-event locator means, said positioning means is used to adjust the angular orientation and linear position of each of said detector modules in space, wherein each of said detector modules is capable of movements which are independent of the remaining detector modules, and said information management means provides repositioning information to the positioning means and further receives information from said positioning means and from said photon event locator means for use in tomographic image reconstruction, wherein during acquisition of tomographic imaging information from the radiation emission source, each of said detector modules moves independently, oscillating through a plurality of linear positions and angular orientations so as to optimize information sampling without orbiting said radiation source.

29. The imaging system of claim 28 wherein said detector modules lie in a first plane and said radiation emission source lies in said first plane, and said detector modules generally surround said emission source.

30. The imaging system of claim 29 wherein each of said detector modules are provided with a combination of angular and linear oscillations using said positioning means so as to acquire views of the emission source from multiple locations and viewing angles.

31. The imaging system of claim 30 wherein the arrangement of said detector modules is in the form of a closed curve.

32. The imaging system of claim 31 wherein the arrangement of said detector modules is in the form of a circle.

33. The imaging system of claim 28 wherein a plurality of detector modules lie in each of plural parallel planes, said detector modules within a given plane forming a closed curve, said closed curves being generally coaxial to form a tubular structure having an interior portion and an exterior portion, said tubular structure receiving said radiation emission source within the interior portion.

34. The imaging system of claim 33 wherein each of said detector modules is provided with angular oscillations using said positioning means so as to acquire views of the emission source from multiple locations and viewing angles.

35. The imaging system of claim 28 wherein the detector modules lie in a first plane and said radiation emission source does not lie in said first plane, and said detector modules generally surround a normal to the first plane which intersects said radiation emission source.

36. The imaging system of claim 35 wherein each of said detector modules are provided with a combination of angular and linear oscillations using said positioning means so as to acquire views of the emission source from multiple locations and viewing angles.

37. The imaging system of claim 36 wherein the arrangement of said detector modules is in the form of a closed curve.

38. The imaging system of claim 37 wherein the arrangement of said detector modules is in the form of a circle.

39. The imaging system of claim 36 wherein the arrangement of detector modules is in the form of multiple closed curves.

40. The imaging system of claim 39 wherein the multiple closed curves are placed side by side within said first plane.

41. The imaging system of claim 39 wherein the multiple closed curves are placed concentrically so as to share a common axis within said first plane.

42. The imaging system of claim 28 wherein the detector modules lie on a topological manifold and said radiation emission source lies adjacent said topological manifold but does not intersect said topological manifold.

43. The imaging system of claim 42 wherein each of said detector modules are provided with a combination of angular and linear oscillations using said positioning means so as to acquire views of the emission source from multiple locations and viewing angles.

44. The imaging system of claim 43 wherein the topological manifold fully surrounds said radiation emission source.

45. The imaging system of claim 43 wherein the topological manifold partially surrounds said radiation emission source.

46. The imaging system of claim 43 wherein the detector modules are maintain on the topological manifold using a mounting means.

47. The imaging system of claim 46 wherein the mounting means is a harness.

48. The imaging system of claim 47 wherein the harness is rigid.

49. The imaging system of claim 47 wherein the harness is semi-rigid.

50. The imaging system of claim 47 wherein the harness is flexible.

51. An imaging system for acquisition of tomographic emission data from an emission source, the imaging system comprising an imaging device and an emission source, the imaging device comprising a plurality of detector modules, module positioning means, and a means for acquiring data, wherein each detector module comprises a radiation detector and a collimator, a plurality of said detector modules and the emission source lie within a single plane and the plurality of detector modules are positioned and oriented such that the emission source is surrounded by and viewed by the plurality of detector modules, the module positioning means providing means for adjusting the position and orientation of each detector module during said acquisition of tomographic emission data so that the position of each detector module can be varied by a combination of translational and rotational motions such that each detector module has the ability to view the radiation source from a plurality of positions and directions and the ability to move independently of other detector modules without orbiting said radiation source, and the data comprises radiation emission data and information regarding the position and orientation of each detector module.

52. An imaging system for acquisition of tomographic emission data from an emission source, the imaging system comprising an imaging device and an emission source, the imaging device comprising a plurality of detector modules, module positioning means, and means for acquiring data, wherein each detector module comprises a radiation detector and a collimator, the plurality of detector modules lies in a first plane and the emission source does not lie within said first plane, and wherein the plurality of detector modules are positioned and oriented within the first plane such that the emission source is surrounded by and viewed by the plurality of detector modules, the module positioning means provides a means for independently adjusting the position and orientation of each detector module during said acquisition of tomographic emission data so that the position and orientation of each of the detector modules can be varied by a combination of translational motions within the first plane and by rotational motions about any of three orthogonal axes defined by the first plane and a normal to the first plane such that the detector module has the ability to view the radiation source from a plurality of positions and directions without orbiting said radiation source and the ability to move independently of other detector modules, and the data comprises radiation emission data and information regarding the position and orientation of each detector module.

53. An imaging system for acquisition of tomographic emission data from an emission source, the imaging system comprising an imaging device and an emission source, the imaging device comprising a plurality of detector modules, module positioning means, and means for acquiring data, wherein each detector module comprises a radiation detector and a collimator, the plurality of detector modules lies within a first non planar surface and the emission source lies at a location which does not intersect first non planar surface, wherein the plurality of detector modules are positioned and oriented within the first non planar surface such that the emission source is surrounded by and viewed by the plurality of detector modules, the module positioning means providing means for adjusting the position and orientation of each detector module during said acquisition of tomographic emission data so that during said acquisition of tomographic emission data each detector module has the ability to view the radiation source from a plurality of positions and directions without orbiting said radiation and the ability to move independently of other detector modules, and so that the position and orientation of each of the detector modules can be independently varied by a) translational motions within the first non planar surface, b) by rotational motions about any of three orthogonal axes, the three orthogonal axes intersecting at the location of a detector module and defined by a normal to the first non planar surface and a plane which is tangent to the non planar surface at a point coincident with a detector module, and c) by a combination of said translational and rotational motions, wherein the data comprises radiation emission data and information regarding the position and orientation of each detector module.

54. An imaging system to acquire tomographic emission data, the system comprising an imaging device and a radiation emission source, the imaging system comprising a plurality of detector modules, module positioning means, module position sensing means and data acquisition means, wherein the detector modules comprise a radiation detector and a collimator, the detector modules are arranged to form a tubular array by providing a plurality of sets of detector modules, each set of detector modules of said plurality of sets arranged to form a planar closed curve, the planar closed curves being stacked to form the tubular array, the tubular array having a longitudinal axis, an interior side, and an exterior side, the module positioning means being attached to the tubular array on said exterior side, and enabling multiple degrees of rotation and translation of each of the detector modules, wherein during acquisition of tomographic emission data from the radiation emission source, each of said detector modules moves independently through a plurality of translations and rotations so as to achieve optimum data acquisition without orbiting said radiation source, the radiation detector and collimator being oriented on the detector modules such that they reside on the interior side of the tubular array; and the emission source placed within the interior side of the tubular array.

55. A method for using an imaging system for imaging a radiation emitting source located within a human being, the imaging system comprising an imaging device and a radiation emission source, the imaging device comprising a plurality of radiation detector modules, module positioning means, and means for acquiring data, wherein each detector module contains a radiation detector and a collimator, the module positioning means providing means for adjusting the position and viewing angle of each detector module so that each detector module has the ability to view the radiation source from a plurality of positions and angular directions and the ability to move independently of other detector modules, and wherein data comprises radiation emission data and information regarding the position and orientation of each detector module, the method steps comprising, 1 placement of a radiation emitting source within a human being, 2 arrangement of said radiation detector modules about said radiation emitting source such that the geometry of the arrangement is known, 3 adjusting the position and viewing angle of each detector module without orbiting, said radiation emission source while concurrently acquiring data, 4 reconstruction of an image of the radiation emission source using the acquired data.

56. The method of claim 55 wherein placement of a radiation emitting source is comprised of administration of a radioisotope.

57. The method of claim 55 wherein the radiation detector modules partially enclose the radiation emitting source.

58. The method of claim 55 wherein the radiation detector modules fully enclose the radiation emitting source.

59. The method of claim 55 wherein a further method step comprises calibration of said radiation detector modules, wherein calibration comprises utilizing known distributions of a radiation emitting source to generate calibration data sets, which are then used to produce and update corrections for the data.

60. The method of claim 56 wherein a further method step is inserted following step 3 wherein the is arrangement of said radiation detector modules about said radiation emitting source is changed to a second arrangement about said radiation emitting source such that the geometry of the second arrangement is known.

61. An imaging system for detection and analysis of tomographic emission data from a radiation source, the imaging system comprising a plurality of individual detector modules, each individual detector module of said plurality of individual detector modules comprising a radiation detector and a collimator, module mounting means, and means for acquiring tomographic emission data, wherein data comprises radiation emission data and information regarding the position and orientation of each individual detector module of said plurality of detector modules, wherein module mounting means comprises means for controlling the translational position and angular orientation of each individual detector module of said plurality of individual detector modules, such that each individual detector module of said plurality of individual detector modules has a translational position and an angular orientation which is independently movable relative to the remaining individual detector modules, wherein module mounting means further comprises means for supporting the plurality of individual detector modules in space, wherein during the collection of tomographic emission data from a radiation source said module mounting means does not orbit about said radiation source, and wherein during the collection of tomographic emission data from a radiation source each individual detector module translates and angulates through a range of localized positions so as to be able to produce a computed tomographical image of the radiation source.

62. The imaging system of claim 61, wherein the position and orientation of each individual detector module of said plurality of individual detector modules can be varied by single axis rotational motions.

63. The imaging system of claim 61 wherein the position and orientation of each individual detector module of said plurality of individual detector modules can be varied by means of multi-axis rotational motions.

64. The imaging system of claim 61 wherein the position and orientation of each individual detector module of said plurality of individual detector modules can be varied by means of rotational motions.

65. The imaging system of claim 61 wherein the position and orientation of each individual detector module of said plurality of individual detector modules can be varied be means of a combination of multi-axis rotational motions and translational motions.

66. The imaging system of claim 65 wherein said multi-axis rotational motions and translational motions are oscillatory.

67. The imaging system of claim 61 wherein the translational and angulations of each of said individual detector modules is related to and synchronized with said collection of tomographic emission data such that said translations and angulations are accomplished in increments of the total required motion, each of said individual detector modules pausing between said increments, and said acquisition of said emission data occurring, during said phase so as to generate a "point-and-shoot" pattern of data acquisition.

68. The imaging system of claim 61 wherein the translations and angulations of each of said individual detector modules is related to and synchronized with said collection of tomographic emission data such that said translations and angulations are accomplished in increments of the total required motion, each of said individual detector modules pausing between said increments, and said acquisition of said emission data occurring during said incremental translation and angulation.

69. The imaging system of claim 61 wherein the translations and angulations of each of said individual detector modules is related to and synchronized with said collection of tomographic emission data such that said translations and angulations are accomplished in increments of the total required motion, each of said individual detector modules pausing between said increments, and said acquisition of said emission data occurring both during said incremental translation and angulation and during said pause.

70. The imaging system of claim 61 wherein the translations and angulations of each of said individual detector modules is related to and synchronized with said collection of tomographic emission data such that said translations and angulations are accomplished using oscillations of each of said individual detector modules, said acquisition of said emission data occurring during said oscillatory translations and angulations.

71. The imaging system of claim 61 wherein the module mounting means is rigid.

72. The imaging system of claim 61 wherein the module mounting means is flexible.

73. The imaging system of claim 61 wherein the module mounting means enables rearrangement of the plurality of detector modules during and between data acquisition.

74. A non-orbiting data acquisition and imaging system for the collection and display tomographic emission data from a radiation source,
   said radiation source being located in and surrounded by a first reference volume, said reference volume having a first reference frame which is fixed and non-moving,
   said non-orbiting data acquisition and imaging system comprising a plurality of individual detector modules, each individual detector module of said plurality of individual detector modules comprising a radiation detector, a collimator, and a module mounting means,
   said non-orbiting data acquisition and imaging system comprising further comprising means for acquiring tomographic emission data, wherein tomographic emission data comprises radiation emission data and information regarding the position and orientation of each individual detector module of said plurality of detector modules,
   said module mounting means comprising a plurality of second reference frames, each of said second reference frames beings fixed relative to said module mounting means and being movable relative to said first reference frame,
   each individual detector module of said plurality of individual detector modules comprising a plurality of third reference frames, one of said plurality of third reference frames being fixed relative each individual detector module such that each individual detector module has an associated third reference frame, each of said plurality of third reference frames being moveable relative to said first reference frame and each of said plurality of second reference frames,
   wherein during acquisition of tomographic emission data by said non-orbiting data acquisition and imaging system, each of said plurality of second reference frames is moveable relative to said first reference frame such that the relative locations of each individual detector module of said plurality of detector modules may be moved with respect to other individual detector modules, and said plurality of second reference frames does not orbit said first reference volume,
   wherein during acquisition of tomographic emission data by said non-orbiting data acquisition and imaging system, said plurality of third reference frames are not fixed relative to said plurality of second reference frames such that each individual detector module of said plurality of detector modules is capable of independent translations and angulations relative to said mounting means and said plurality of third reference frames do not orbit said first reference volume.

75. The non-orbiting data acquisition and imaging system of claim 74 wherein each of said plurality of third reference frames being provided with six independent degrees of motion such that each individual detector module is capable of three orthogonal rotations and three orthogonal translations.

76. The non-orbiting data acquisition and imaging system of claim 74 wherein said independent translations and angulations of said plurality of third reference frames are oscillatory.

77. An imaging system to acquire tomographic emission data, the system comprising an imaging device and a radiation emission source, the imaging device comprising a plurality of independent detector modules, each independent detector module having module positioning means module position sensing means, and data acquisition means, wherein
   each independent detector module comprises a radiation detector and a collimator,
   the plurality of independent detector modules are arranged by providing a plurality of sets of detector modules, each set of detector modules of said plurality of sets of detector modules arranged to form a closed curve, each closed curve having a centroid, the centroid of each closed curve being contained in an axial centroid line, the closed curves forming a surface having an interior surface and an exterior surface,
   the module positioning means being attached to each closed curve on said exterior surface, and enabling multiple degrees of rotation and translation of each of the detector modules, wherein during acquisition of tomographic emission data from the radiation emission source, each of said detector modules moves independently through a plurality of translations and rotations so as to achieve optimum data acquisition without orbiting said radiation source,
   the radiation detector and collimator being oriented on the detector modules such that they reside on the interior surface, and the emission source residing within the interior surface.

78. The imaging system of claim 77 wherein said closed curves are circular in shape.

79. The imaging system of claim 77 wherein said closed curves are non-planar.

80. The imaging system of claim 77 wherein said centroids of said closed curves are coincident.

81. The imaging system of claim 77 wherein said centroids of said closed curves are distributed along said centroid line such that the centroids are spaced apart from each other.

82. The imaging system of claim 77 wherein said centroid line is a straight line.

83. The imaging system of claim 77 wherein said centroid line is a curved (non-straight) line.

84. The imaging system of claim 77 wherein each of said sets of detector modules is arranged to form one or more arc segments on its respective said closed curve.

85. An imaging system to acquire tomographic emission data, the system comprising an imaging device and a radiation emission source, the imaging device comprising a plurality of independent detector modules, each independent detector module having module positioning means, module positioning means, and data acquisition means, wherein each independent detector module comprises a radiation detector and a collimator, the plurality of independent detector modules are arranged by providing a plurality of sets of detector modules, each set of detector modules of said plurality of sets of detector modules arranged to form a closed curve, each closed curve having a centroid, the centroid of each closed curve being contained in a centroid surface, the centroid surface having an inferior side and a superior side, the module positioning means being attached to each independent detector module on said superior side and enabling multiple degrees of rotation and translation of each of the independent detector modules, wherein during acquisition of tomographic emission data from the radiation emission source, each of said independent detector modules moves independently through a plurality of translations and rotations so as to achieve optimum data acquisition without orbiting said radiation source, the radiation detector and collimator being oriented on the independent detector modules such that they reside on the inferior side of said centroid surface, and the emission source residing below the inferior side of said centroid surface.

86. The imaging system of claim 85 wherein said closed curves are circular in shape.

87. The imaging system of claim 85 wherein said closed curves are non-planar.

88. The imaging system of claim 85 wherein said centroids of said closed curves are coincident.

89. The imaging system of claim 85 wherein said centroids of said closed curves are distributed within the centroid frame such that the centroids are spaced apart from each other.

90. The imaging system of claim 85 wherein said centroid surface is a planar.

91. The imaging system of claim 85 wherein said centroid surface is non-planar.

92. The imaging system of claim 55 wherein each of said set of detector modules is arranged to form one or more arc segments on its respective said closed curve.

* * * * *